United States Patent
Sandberg et al.

(10) Patent No.: US 11,045,558 B2
(45) Date of Patent: *Jun. 29, 2021

(54) RPGR GENE THERAPY FOR RETINITIS PIGMENTOSA

(71) Applicants: MASSACHUSETTS EYE & EAR INFIRMARY, Boston, MA (US); UCL BUSINESS LTD., London (GB); The Govt. of the USA, as represented by the Secy., Dept. of Health and Human Services, Bethesda, MD (US)

(72) Inventors: Michael A. Sandberg, Reading, MA (US); Basil Pawlyk, Hampton Falls, NH (US); Alan Finlay Wright, Edinburgh (GB); Xinhua Shu, Glasgow (GB); Tiansen Li, Clarksburg, MD (US); Robin Ali, London (GB)

(73) Assignees: Massachusetts Eye & Ear Infirmary, Boston, MA (US); UCL Business Ltd., London (GB); The Government of the United States of America, as represented by the Secretary, Department of Health and Human Services, Bethesda, MD (US)

( * ) Notice: Subject to any disclaimer, the term of this patent is extended or adjusted under 35 U.S.C. 154(b) by 43 days.

This patent is subject to a terminal disclaimer.

(21) Appl. No.: 16/436,521

(22) Filed: Jun. 10, 2019

(65) Prior Publication Data

US 2020/0215203 A1 Jul. 9, 2020

Related U.S. Application Data

(63) Continuation of application No. 15/328,617, filed as application No. PCT/US2015/040866 on Jul. 17, 2015, now Pat. No. 10,314,924.

(60) Provisional application No. 62/028,638, filed on Jul. 24, 2014.

(51) Int. Cl.
   *A61K 48/00* (2006.01)
   *C07K 14/47* (2006.01)
   *A61K 9/00* (2006.01)

(52) U.S. Cl.
   CPC .......... *A61K 48/005* (2013.01); *A61K 9/0048* (2013.01); *C07K 14/4702* (2013.01); *C12N 2750/14143* (2013.01)

(58) Field of Classification Search
   CPC .................................................. A61K 48/005
   See application file for complete search history.

(56) References Cited

U.S. PATENT DOCUMENTS

| 4,868,116 | A | 9/1989 | Morgan et al. |
| 4,980,286 | A | 12/1990 | Morgan et al. |
| 5,767,079 | A | 6/1998 | Glaser et al. |
| 9,770,491 | B2 | 9/2017 | Beltran et al. |
| 10,314,924 | B2 * | 6/2019 | Sandberg ........... C07K 14/4702 |

FOREIGN PATENT DOCUMENTS

| WO | 89/02468 A1 | 3/1989 |
| WO | 89/05345 A1 | 6/1989 |
| WO | 89/07136 A2 | 8/1989 |
| WO | 92/07573 A1 | 5/1992 |
| WO | 2001/038578 A1 | 5/2001 |
| WO | 2001/077380 A2 | 10/2001 |
| WO | 2014/011210 A1 | 1/2014 |
| WO | 2016/001693 A1 | 1/2016 |

OTHER PUBLICATIONS

Acland, G.M. et al., "Gene Therapy Restores Vision in a Canine Model of Childhood Blindness"; Nat Genet (2001); vol. 28; pp. 92-5.
Alexander, J.J. et al., "Restoration of Cone Vision in a Mouse Model of Achromatopsia"; Nat Med (2007); vol. 13; pp. 685-7.
Ali, R.R. et al., "Restoration of Photoreceptor Ultrastructure and Function in Retinal Degeneration Slow Mice by Gene Therapy", Nat Genet (2000); vol. 25; pp. 306-10.
Allocca, M. et al., "Novel Adeno-Associated Virus Serotypes Efficiently Transduce Marine Photoreceptors", J. Virol (2007); vol. 81; pp. 11372-80.
Bader, I. et al., "X-Linked Retinitis Pigmentosa: RPGR Mutations in Most Families With Definite X Linkage and Clustering of Mutations in a Short Sequence Stretch of Exon ORF15", Invest Ophthalmol Vis Sci (2003); vol. 44; pp. 1458-63.
Bainbridge, J.W. et al., "Effect of Gene Therapy on Visual Function in Leber's Congenital Amaurosis", N. Engl J Med (2008); vol. 358; pp. 2231-9.
Beltran, W.A. et al., "Gene Therapy Rescues Photoreceptor Blindness in Dogs and Paves the Way for Treating Human X-Linked Retinitis Pigmentosa", PNAS USA (2012); vol. 109; pp. 2132-7.
Berson, E.L. et al., "Retinitis pigmentosa. The Friedenwald Lecture." Invest Ophthalmol Vis Sci (1993); vol. 34; pp. 1659-76.
Boylan, J.P. et al., "Identification of a Novel Protein Interacting With RPGR", Hum Mol Genet (2000); vol. 9; pp. 2085-2093.
Branham, K et al., "Mutations in RPGR and RP2 Account for 15% of Males with Simplex Retinal Degenerative Disease", Invest Ophthalmol Vis Sci (2012); vol. 53; pp. 8232-7.
Breuer, D.K. et al., "A Comprehensive Mutation Analysis of RP2 and RPGR in a North American Cohort of Families with X-Linked Retinitis Pigmentosa"; Am J Hum Genet (2002); vol. 70; pp. 1545-54.

(Continued)

*Primary Examiner* — Scott Long
(74) *Attorney, Agent, or Firm* — Fox Rothschild LLP

(57) ABSTRACT

Methods for treating a human subject who has X-linked Retinitis Pigmentosa (XLRP) or another clinically-defined ophthalmological condition due to a loss-of-function mutation in the gene encoding the retinitis pigmentosa GTPase regulator (RPGR) protein, the method comprising administering to the subject a nucleic acid comprising an adeno-associated viral vector comprising an abbreviated human RPGR cDNA.

23 Claims, 10 Drawing Sheets

Specification includes a Sequence Listing.

(56) References Cited

OTHER PUBLICATIONS

Churchill, J.D. et al., "Mutations in the X-Linked Retinitis Pigmentosa Genes RPGR and RP2 Found in 8.5% of Families With a Provisional Diagnosis of Autosomal Dominant Retinitis Pigmentosa", Invest Ophthalmol Vis Sci (2013); vol. 54; pp. 1411-6.
Cideciyan, A.V. et al., "Human Gene Therapy for RPE65 Isomerase Deficiency Activates the Retinoid Cycle of Vision but With Slow Rod Kinetics"; Proc Natl Acad Sci U S A (2008); vol. 105; pp. 15112-7.
Hong, D. H, et al., "Complex Expression Pattern of RPGR Reveals a Role for Purine-Rich Exonic Splicing Enhancers"; Invest Ophthalmol Vis Sci (2002); vol. 43; pp. 3373-82.
Hong, D. H. et al., "RPGR Isoforms in Photoreceptor Connecting Cilia and the Transitional Zone of Motile Cilia"; Invest Ophthalmol Vis Sci (2003); vol. 44; pp. 2413-21.
Hong, D. H. et al., "A Single, Abbreviated RPGR-ORF15 Variant Reconstitutes RPGR Function in Vivo". Invest Ophthalmol Vis Sci (2005); vol. 46; pp. 435-41.
Hong D.H., et al., "A Retinitis Pigmentosa Gtpase Regulator (RPGR)-Deficient Mouse Model for X-Linked Retinitis Pigmentosa (RP3)"; Proc Natl Acad Sci USA (2000); vol. 97; pp. 3649-54.
Hong, D. H., et al., Retinitis Pigmentosa Gtpase Regulator (RPGR)-Interacting Protein is Stably Associated with the Photoreceptor Ciliary Axoneme and Anchors RPGR to the Connecting Cilium; J Biol Chem (2001); vol. 276; pp. 12091-12099.
Jacobi, F. K. et al., "Mutational Risk in Highly Repetitive Exon ORF15 of the RPGR Multidisease Gene Is Not Associated With Haplotype Background"; Int J Mol Med (2005); vol. 16; pp. 1175-8.
Karra, D. et al. "Population Haplotypes of Exon ORF15 of the Retinitis Pigmentosa Gtpase Regulator Gene in Germany: Implications for Screening for Inherited Retinal Disorders"; Mol Diagn Ther (2006); vol. 10; pp. 115-23.
Khani, S. C., et al., "AAV-Mediated Expression Targeting of Rod and Cone Photoreceptors with a Human Rhodopsin Kinase Promoter"; Invest Ophthalmol Vis Sci (2007); vol. 48; pp. 3954-61.
Komaromy, A. M., et al., "Gene Therapy Rescues Cone Function in Congenital Achromatopsia"; Hum Mol Genet (2010); vol. 19; pp. 2581-93.
Lheriteau, E. et al., "The RPGRIP1-Deficient Dog, A Promising Canine Model for Gene Therapy"; Mol Vis (2009); vol. 15; pp. 349-61.
MacLaren, R. E. et al., Retinal Gene Therapy in Patients with Choroideremia: Initial Findings from a Phase 1/2 Clinical Trial. Lancet (2014).
Maguire, A.M. et al., "Safety and Efficacy of Gene Transfer for Leber's Congenital Amaurosis"; N Engl J Med (2008); vol. 358; pp. 2240-8.
Natkunarajah, M. et al. "Assessment of Ocular Transduction Using Single-Stranded and Self-Complementary Recominant Adeno-Associated Virus Serotype 2/8"; Gene Ther (2008); vol. 358; pp. 2240-8.
Pang, J. J., et al., "AAV-Mediated Gene Therapy in Mouse Models of Recessive Retinal Degeneration"; Curr Mol Med (2012); vol. 12; pp. 316-30.
Pawlyk, B.S. et al., "Replacement Gene Therapy with a Human RPGRIP1 Sequence Slows Photoreceptor Degeneration in a Murine Model of Leber Congenital Amaurosis"; Hum Gene Ther (2010); vol. 21; pp. 993-1004.
Pawlyk, B.S., et al. "Gene Replacement Therapy Rescues Photoreceptor Degeneration in a Murine Model of Leber Congenital Amaurosis Lacking RPGRIP"; Invest Ophthalmol Vis Sci (2005); vol. 46; pp. 3039-45.
Pelletier, V., et al. "Comprehensive Survey of Mutations in RP2 and RPGR in Patients Affected With Distinct Retinal Dystrophies: Genotype-Phenotype Correlations and Impact on Genetic Counseling"; Hum Mutat (2007); vol. 28; pp. 81-91.
Roepman, R. et al., "The Retinitis Pigmentosa Gtpase Regulator (RPGR) Interacts with Novel Transport-Like Proteins in the Outer Segments of Rod Photoreceptors"; Hum Mol Genet (2000); vol. 9; pp. 2095-2105.
Sandberg, et al., "Disease Course of Patients with X-Linked Retinitis Pigmentosa due to RPGR Gene Mutations"; Invest Ophthalmol Vis Sci (2007); vol. 48; pp. 1298-304.
Sun, X., et al. "Gene Therapy with a Promoter Targeting Both Rods and Cones Rescues Retinal Degeneration Caused by AIPL1 Mutations"; Gene Ther (2010); vol. 17; pp. 117-131.
Tan, M.H. et al., "Gene Therapy for Retinitis Pigmentosa and Leber Congenital Amaurosis Caused by Defects in AIPL1: Effective Rescue of Mouse Models of Partial and Complete Aipll Deficiency Using AAV2/2 and AAV2/8 Vectors"; Hum Mol Genet (2009).
Thompson, D.A. et al., Rd9 is a Naturally Occurring Mouse Model of a Common form of Retinitis Pigmentosa Caused by Mutations in RPGR-ORF15. PLoS One (2012); vol. 7; p. e35865.
Vervoort, R. et al., "Mutational hot spot within a new RPGR exon in X-linked retinitis pigmentosa"; Nature Genetics(2000); vol. 25; pp. 462-466.
Vervoort, R, "Mutations of RPGR in X-Linked Retinitis Pigmentosa (RP3)"; Hum Mutat (2002). vol. 19; pp. 486-500.
Yang J. et al., "Rootletin, a novel coiled-coil protein, is a structural component of the ciliary rootlet"; J Cell Biol (2002); vol. 159; pp. 431-440.
Shu, X. et al., "RPGR ORF15 Isoform Co-Localizes with RPGRIP1 at Centrioles and Basal Bodies and Interacts with Nucleophosmin"; Human Molecular Genetics (2005); vol. 14:9; pp. 1183-1197.
Pawlyk, B.S. et al., "Photoreceptor rescue by an abbreviated human RPGR gene in a murine model of X-linked retinitis Pigmentosa" Gene Therapy (2016); vol. 23:2; pp. 196-204.
Kolb, H. "Simple Anatomy of the Retina"; Webvision (2011); pp. 1-12.
Hong, D. et al., "A Single, Abbreviated RPGR-ORF15 Variant Reconstitutes BPGR Function in Vivo"; Ophthalmology & Visual Science (2005); vol. 46:2, pp. 435-41.
Pawlyk, B.S. et al., "Photorecptor Rescure by an Abbreviated Human RPGR Gene in a Murine Model of X-linked Retinitis Pigmentosa"I Gene Therapy (2016); vol. 23:2; pp. 196-204.
Extended European Search Report and Written Opinion from relatated European Patent Application No. 158253381. dated Nov. 12, 2017, 11 pgs.

\* cited by examiner

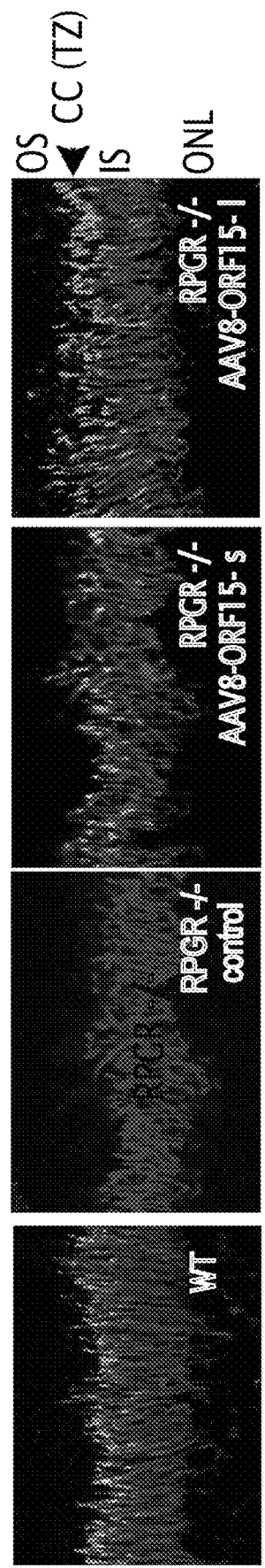
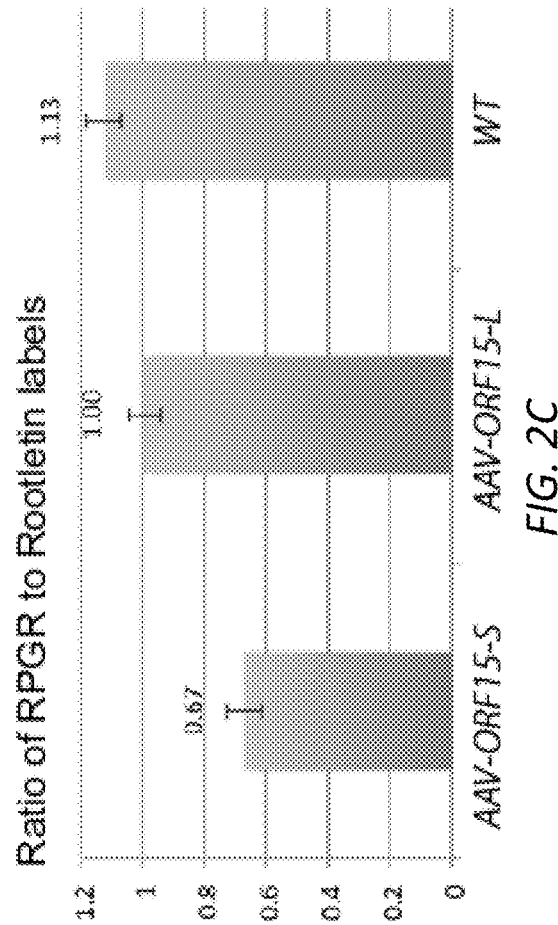
FIG. 2B
FIG. 2C

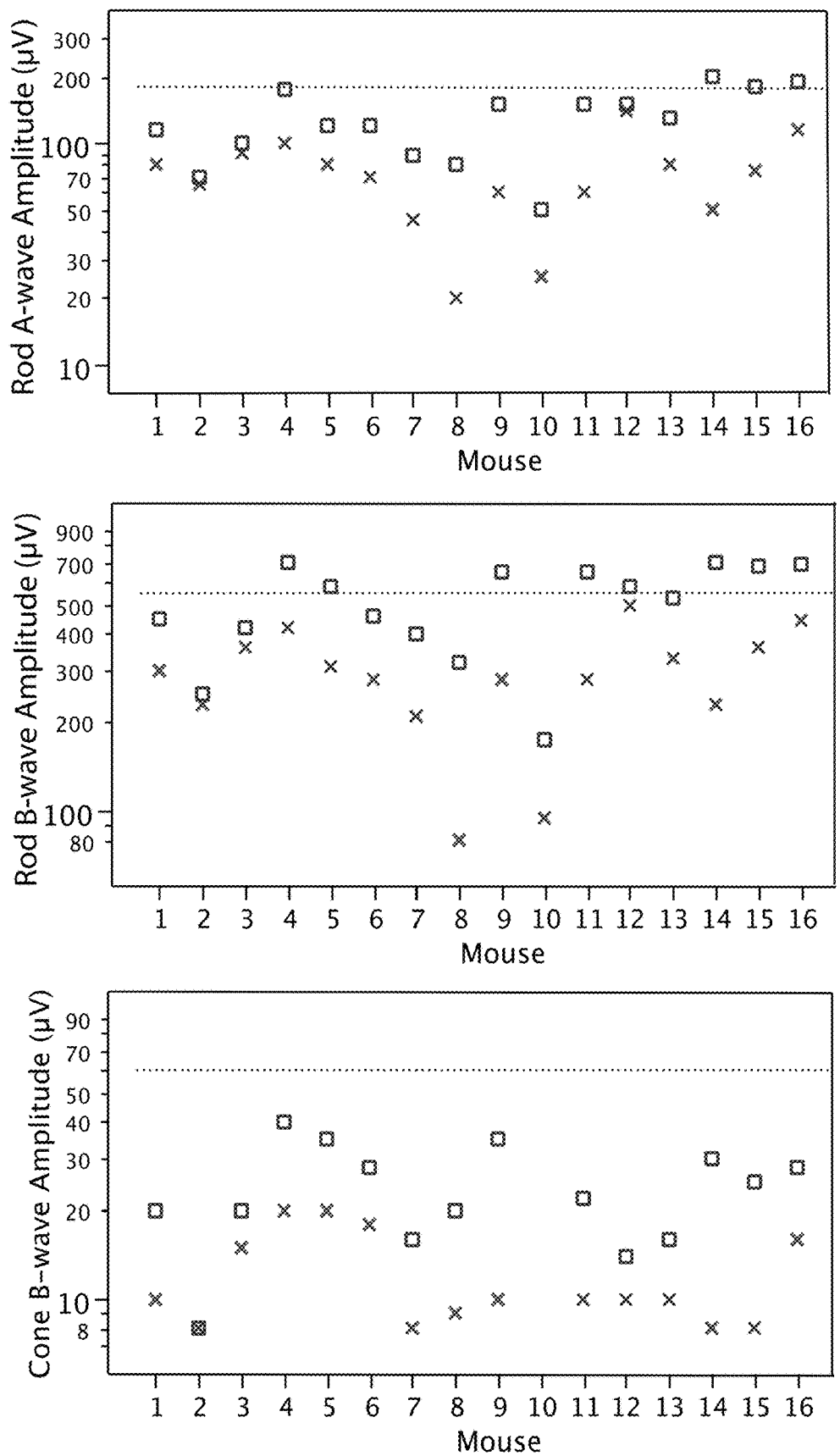
FIG. 5A  × OD  □ OS  ······· WT Lower Limit

SEQUENCE LISTING

```
<160> NUMBER OF SEQ ID NOS: 5

<210> SEQ ID NO 1
<211> LENGTH: 3081
<212> TYPE: DNA
<213> ORGANISM: Artificial Sequence
<220> FEATURE:
<223> OTHER INFORMATION: Human RPGRORF15 sequence with 378bp deleted

<400> SEQUENCE: 1
atgagggagc cggaagagct gatgcccgat tcgggtgctg tgtttacatt tgggaaaagt      60
aaatttgctg aaaataatcc cggtaaattc tggtttaaaa atgatgtccc tgtacatctt     120
tcatgtggag atgaacattc tgctgttgtt accggaaata ataaacttta catgtttggc     180
agtaacaact ggggtcagtt aggattagga tcaaagtcag ccatcagcaa gccaacatgt     240
gtcaaagctc taaaacctga aaaagtgaaa ttagctgcct gtggaaggaa ccacaccctg     300
gtgtcaacag aaggaggcaa tgtatatgca actggtggaa ataatgaagg acagttgggg     360
cttggtgaca ccgaagaaag aaacactttt catgtaatta gctttttac atccgagcat     420 aagattaagc agctgtctgc tggatctaat acttcagctg ccctaactga ggatggaaga     480 cttttttatgt ggggtgacaa ttccgaaggg caaattggtt taaaaaatgt aagtaatgtc     540
tgtgtccctc agcaagtgac cattgggaaa cctgtctcct ggatctcttg tggatattac     600
cattcagctt ttgtaacaac agatggtgag ctatatgtgt tggagaacc tgagaatggg     660
```

```
aagttaggtc ttcccaatca gctcctgggc aatcacagaa cacccagct ggtgtctgaa      720
attccggaga aggtgatcca agtagcctgt ggtggagagc atactgtggt tctcacggag      780
aatgctgtgt atacctttgg gctgggacaa tttggtcagc tgggtcttgg cacttttctt      840
tttgaaactt cagaacccaa agtcattgag aatattaggg atcaaacaat aagttatatt      900
tcttgtggag aaaatcacac agctttgata acagatatcg gccttatgta tacttttgga      960
gatggtcgcc acgaaaaatt aggacttgga ctggagaatt ttaccaatca cttcattcct     1020
actttgtgct ctaattttt gaggtttata gttaaattgg ttgcttgtgg tggatgtcac      1080
atggtagttt ttgctgctcc tcatcgtggt gtggcaaaag aaattgaatt cgatgaaata     1140
aatgatactt gcttatctgt ggcgactttt ctgccgtata gcagtttaac ctcaggaaat     1200
gtactgcaga ggactctatc agcacgtatg cggcgaagag agaggagag gtctccagat      1260
tctttttcaa tgaggagaac actacctcca atagaaggga ctcttggcct ttctgcttgt     1320
tttctcccca attcagtctt tccacgatgt tctgagagaa acctccaaga gagtgtctta    1380
tctgaacagg acctcatgca gccagaggaa ccagattatt tgctagatga aatgaccaaa     1440
gaagcagaga tagataattc ttcaactgta gaaagccttg gagaaactac tgatatctta     1500
aacatgacac acatcatgag cctgaattcc aatgaaaagt cattaaaatt atcaccagtt     1560
cagaaacaaa agaaacaaca aacaattggg gaactgacgc aggatacagc tcttactgaa     1620
aacgatgata gtgatgaata tgaagaaatg tcagaaatga agaagggaa agcatgtaaa      1680
caacatgtgt cacaagggat tttcatgacg cagccagcta cgactatcga agcattttca     1740
gatgaggaag tagagatccc agaggagaag gaaggagcag aggattcaaa aggaaatgga     1800
atagaggagc aagaggtaga agcaaatgag gaaaatgtga aggtgcatgg aggaagaaag     1860
gagaaaacag agatcctatc agatgacctt acagacaaag cagaggtgag tgaaggcaag     1920
gcaaaatcag tgggagaagc agaggatggg cctgaaggta gagggatgg aacctgtgag     1980
gaaggtagtt caggagcaga acactggcaa gatgaggaga gggagaaggg ggagaaagac     2040
aagggtagag gagaaatgga gaggccagga gagggagaga aggaactagc agagaaggaa     2100
gaatggaaga agagggatgg ggaagagcag gagcaaaagg agagggagca gggccatcag     2160
aaggaaagaa accaagagat ggaggaggga ggggaggagg agcatggaga aggagaagaa     2220
gaggagggag acagagaaga ggaagaagag aaggaggag aagggaaaga ggaaggagaa      2280
ggggaagaag tggagggaga acgtgaaaag gaggaaggag agaggaaaaa ggaggaaaga     2340
gcggggaagg aggagaaagg agaggaagaa ggagaccaag gagaggggga agaggaggaa     2400
acagagggga gagggaggaa aaagaggag ggagggaag tagagggagg ggaagtagag       2460
gaggggaaag gagagaggga agaggaagag gaggagggtg aggggaaga gaggaagggg      2520
gagggggaag aggaggaagg ggaggggaa gaggaggaag gagaagggaa aggggaggaa      2580
gaaggggagg gggaagagga ggaagggaa gaagaagggg aggaagaagg agagggagag     2640
gaagaagggg agggagaagg ggaggaagaa gaggaagggg aagtggaagg ggaggtggaa     2700
ggggaggaag gagaggggga aggagaggaa gaggaaggag aggaggaagg agaagaaagg     2760
gaaaaggagg gggaaggaga agaaaacagg aggaacagag aagaggagga ggaagaagag     2820
gggaagtatc aggagacagg cgaagaagag aatgaaaggc aggatggaga ggagtacaaa     2880
aaagtgagca aaataaaagg atctgtgaaa tatggcaaac ataaaacata tcaaaaaaag     2940
tcagttacta acacacaggg aaatgggaaa gagcagaggt ccaaaatgcc agtccagtca     3000
```

```
aaacgacttt taaaaaatgg gccatcaggt tccaaaaagt tctggaataa tatattacca    3060
cattacttgg aattgaagta a                                              3081
```

<210> SEQ ID NO 2
<211> LENGTH: 1026
<212> TYPE: PRT
<213> ORGANISM: Artificial Sequence
<220> FEATURE:
<223> OTHER INFORMATION: Human RPGRORF15 sequence with 126 amino acids
      deleted

<400> SEQUENCE: 2

```
Met Arg Glu Pro Glu Leu Met Pro Asp Ser Gly Ala Val Phe Thr
1               5                   10                  15

Phe Gly Lys Ser Lys Phe Ala Glu Asn Asn Pro Gly Lys Phe Trp Phe
                20                  25                  30

Lys Asn Asp Val Pro Val His Leu Ser Cys Gly Asp Glu His Ser Ala
            35                  40                  45

Val Val Thr Gly Asn Asn Lys Leu Tyr Met Phe Gly Ser Asn Asn Trp
        50                  55                  60

Gly Gln Leu Gly Leu Gly Ser Lys Ser Ala Ile Ser Lys Pro Thr Cys
65                  70                  75                  80

Val Lys Ala Leu Lys Pro Glu Lys Val Lys Leu Ala Ala Cys Gly Arg
                85                  90                  95

Asn His Thr Leu Val Ser Thr Glu Gly Gly Asn Val Tyr Ala Thr Gly
            100                 105                 110

Gly Asn Asn Glu Gly Gln Leu Gly Leu Gly Asp Thr Glu Glu Arg Asn
        115                 120                 125

Thr Phe His Val Ile Ser Phe Phe Thr Ser Glu His Lys Ile Lys Gln
    130                 135                 140

Leu Ser Ala Gly Ser Asn Thr Ser Ala Ala Leu Thr Glu Asp Gly Arg
145                 150                 155                 160

Leu Phe Met Trp Gly Asp Asn Ser Glu Gly Gln Ile Gly Leu Lys Asn
                165                 170                 175

Val Ser Asn Val Cys Val Pro Gln Gln Val Thr Ile Gly Lys Pro Val
            180                 185                 190

Ser Trp Ile Ser Cys Gly Tyr Tyr His Ser Ala Phe Val Thr Thr Asp
        195                 200                 205

Gly Glu Leu Tyr Val Phe Gly Glu Pro Glu Asn Gly Lys Leu Gly Leu
    210                 215                 220

Pro Asn Gln Leu Leu Gly Asn His Arg Thr Pro Gln Leu Val Ser Glu
225                 230                 235                 240

Ile Pro Glu Lys Val Ile Gln Val Ala Cys Gly Gly Glu His Thr Val
                245                 250                 255

Val Leu Thr Glu Asn Ala Val Tyr Thr Phe Gly Leu Gly Gln Phe Gly
            260                 265                 270

Gln Leu Gly Leu Gly Thr Phe Leu Phe Glu Thr Ser Glu Pro Lys Val
        275                 280                 285

Ile Glu Asn Ile Arg Asp Gln Thr Ile Ser Tyr Ile Ser Cys Gly Glu
    290                 295                 300

Asn His Thr Ala Leu Ile Thr Asp Ile Gly Leu Met Tyr Thr Phe Gly
305                 310                 315                 320

Asp Gly Arg His Gly Lys Leu Gly Leu Gly Leu Glu Asn Phe Thr Asn
                325                 330                 335

His Phe Ile Pro Thr Leu Cys Ser Asn Phe Leu Arg Phe Ile Val Lys
```

-continued

```
                340                 345                 350
Leu Val Ala Cys Gly Cys His Met Val Phe Ala Ala Pro His
            355                 360                 365
Arg Gly Val Ala Lys Glu Ile Glu Phe Asp Glu Ile Asn Asp Thr Cys
        370                 375                 380
Leu Ser Val Ala Thr Phe Leu Pro Tyr Ser Ser Leu Thr Ser Gly Asn
385                 390                 395                 400
Val Leu Gln Arg Thr Leu Ser Ala Arg Met Arg Arg Arg Glu Arg Glu
                405                 410                 415
Arg Ser Pro Asp Ser Phe Ser Met Arg Arg Thr Leu Pro Pro Ile Glu
            420                 425                 430
Gly Thr Leu Gly Leu Ser Ala Cys Phe Leu Pro Asn Ser Val Phe Pro
        435                 440                 445
Arg Cys Ser Glu Arg Asn Leu Gln Glu Ser Val Leu Ser Glu Gln Asp
    450                 455                 460
Leu Met Gln Pro Glu Glu Pro Asp Tyr Leu Leu Asp Glu Met Thr Lys
465                 470                 475                 480
Glu Ala Glu Ile Asp Asn Ser Ser Thr Val Glu Ser Leu Gly Glu Thr
                485                 490                 495
Thr Asp Ile Leu Asn Met Thr His Ile Met Ser Leu Asn Ser Asn Glu
            500                 505                 510
Lys Ser Leu Lys Leu Ser Pro Val Gln Lys Gln Lys Gln Gln Thr
        515                 520                 525
Ile Gly Glu Leu Thr Gln Asp Thr Ala Leu Thr Glu Asn Asp Asp Ser
    530                 535                 540
Asp Glu Tyr Glu Glu Met Ser Glu Met Lys Glu Gly Lys Ala Cys Lys
545                 550                 555                 560
Gln His Val Ser Gln Gly Ile Phe Met Thr Gln Pro Ala Thr Thr Ile
                565                 570                 575
Glu Ala Phe Ser Asp Glu Glu Val Glu Ile Pro Glu Glu Lys Glu Gly
            580                 585                 590
Ala Glu Asp Ser Lys Gly Asn Gly Ile Glu Glu Gln Glu Val Glu Ala
        595                 600                 605
Asn Glu Glu Asn Val Lys Val His Gly Gly Arg Lys Glu Lys Thr Glu
    610                 615                 620
Ile Leu Ser Asp Asp Leu Thr Asp Lys Ala Glu Val Ser Glu Gly Lys
625                 630                 635                 640
Ala Lys Ser Val Gly Glu Ala Glu Asp Gly Pro Glu Gly Arg Gly Asp
                645                 650                 655
Gly Thr Cys Glu Glu Gly Ser Ser Gly Ala Glu His Trp Gln Asp Glu
            660                 665                 670
Glu Arg Glu Lys Gly Glu Lys Asp Lys Gly Arg Gly Glu Met Glu Arg
        675                 680                 685
Pro Gly Glu Gly Glu Lys Glu Leu Ala Glu Lys Glu Glu Trp Lys Lys
    690                 695                 700
Arg Asp Gly Glu Glu Gln Gln Lys Glu Arg Glu Gln Gly His Gln
705                 710                 715                 720
Lys Glu Arg Asn Gln Glu Met Glu Glu Gly Glu Glu His Gly
                725                 730                 735
Glu Gly Glu Glu Glu Glu Gly Asp Arg Glu Glu Glu Glu Lys Glu
            740                 745                 750
Gly Glu Gly Lys Glu Glu Gly Glu Gly Glu Glu Val Glu Gly Glu Arg
        755                 760                 765
```

Glu Lys Glu Glu Gly Glu Arg Lys Lys Glu Glu Arg Ala Gly Lys Glu
        770                 775                 780

Glu Lys Gly Glu Glu Glu Gly Asp Gln Gly Glu Gly Glu Glu Glu Glu
785                 790                 795                 800

Thr Glu Gly Arg Gly Glu Glu Lys Glu Glu Gly Gly Glu Val Glu Gly
            805                 810                 815

Gly Glu Val Glu Glu Gly Lys Gly Glu Arg Glu Glu Glu Glu Glu Glu
            820                 825                 830

Gly Glu Gly Glu Glu Glu Glu Glu Gly Glu Glu Glu Glu Gly Glu
            835                 840                 845

Gly Glu Glu Glu Glu Gly Glu Gly Lys Gly Glu Glu Glu Gly Glu Gly
        850                 855                 860

Glu Glu Glu Glu Gly Glu Glu Gly Glu Glu Glu Gly Glu Gly Glu
865                 870                 875                 880

Glu Glu Gly Glu Gly Glu Gly Glu Glu Glu Glu Gly Glu Val Glu
            885                 890                 895

Gly Glu Val Glu Gly Glu Glu Gly Glu Glu Glu Gly Glu Glu Glu Glu
            900                 905                 910

Gly Glu Glu Glu Gly Glu Arg Glu Lys Glu Gly Glu Gly Glu Glu
        915                 920                 925

Asn Arg Arg Asn Arg Glu Glu Glu Glu Glu Glu Gly Lys Tyr Gln
    930                 935                 940

Glu Thr Gly Glu Glu Glu Asn Glu Arg Gln Asp Gly Glu Glu Tyr Lys
945                 950                 955                 960

Lys Val Ser Lys Ile Lys Gly Ser Val Lys Tyr Gly Lys His Lys Thr
            965                 970                 975

Tyr Gln Lys Lys Ser Val Thr Asn Thr Gln Gly Asn Gly Lys Glu Gln
        980                 985                 990

Arg Ser Lys Met Pro Val Gln Ser Lys Arg Leu Leu Lys Asn Gly Pro
        995                 1000                1005

Ser Gly Ser Lys Lys Phe Trp Asn Asn Ile Leu Pro His Tyr Leu Glu
        1010                1015                1020

Leu Lys
1025

<210> SEQ ID NO 3
<211> LENGTH: 3459
<212> TYPE: DNA
<213> ORGANISM: Homo sapiens

<400> SEQUENCE: 3
atgagggagc cggaagagct gatgcccgat tcgggtgctg tgtttacatt tgggaaaagt      60
aaatttgctg aaaataatcc cggtaaattc tggtttaaaa atgatgtccc tgtacatctt     120
tcatgtggag atgaacattc tgctgttgtt accggaaata taaactttta catgtttggc     180
agtaacaact ggggtcagtt aggattagga tcaaagtcag ccatcagcaa gccaacatgt     240
gtcaaagctc taaaacctga aaaagtgaaa ttagctgcct gtggaaggaa ccacaccctg     300
gtgtcaacag aaggaggcaa tgtatatgca actggtggaa ataatgaagg acagttgggg     360
cttggtgaca ccgaagaaag aaacactttt catgtaatta gctttttac atccgagcat     420 aagattaagc agctgtctgc tggatctaat acttcagctg ccctaactga ggatggaaga     480
cttttttatg tggggtgaca attccgaaggg caaattggtt taaaaaatgt aagtaatgtc     540
tgtgtccctc agcaagtgac cattgggaaa cctgtctcct ggatctcttg tggatattac     600

```
cattcagctt ttgtaacaac agatggtgag ctatatgtgt ttggagaacc tgagaatggg    660
aagttaggtc ttcccaatca gctcctgggc aatcacagaa cacccagct  ggtgtctgaa    720 attccggaga aggtgatcca agtagcctgt ggtggagagc atactgtggt tctcacggag    780
aatgctgtgt ataccttttgg gctgggacaa tttggtcagc tgggtcttgg cacttttctt    840
tttgaaactt cagaacccaa agtcattgag aatattaggg atcaaacaat aagttatatt    900
tcttgtggag aaaatcacac agctttgata acagatatcg gccttatgta acttttgga    960 gatggtcgcc acggaaaatt aggacttgga ctggagaatt ttaccaatca cttcattcct   1020
actttgtgct ctaattttt  gaggtttata gttaaattgg ttgcttgtgg tggatgtcac   1080
atggtagttt ttgctgctcc tcatcgtggt gtggcaaaag aaattgaatt cgatgaaata   1140
aatgatactt gctatctgt ggcgactttt ctgccgtata gcagtttaac ctcaggaaat    1200
gtactgcaga ggactctatc agcacgtatg cggcgaagag agagggagag gtctccagat   1260 tcttttcaa tgaggagaac actacctcca atagaaggga ctcttggcct ttctgcttgt   1320
tttctcccca attcagtctt tccacgatgt tctgagagaa acctccaaga gagtgtctta   1380
tctgaacagg acctcatgca gccagaggaa ccagattatt tgctagatga aatgaccaaa   1440
gaagcagaga tagataattc ttcaactgta gaaagccttg gagaaactac tgatatctta   1500
aacatgacac acatcatgag cctgaattcc aatgaaaagt cattaaaatt atcaccagtt   1560
cagaaacaaa agaaacaaca acaattgggg gaactgacgc aggatacagc tcttactgaa   1620
aacgatgata gtgatgaata tgaagaaatg tcagaaatga agaagggaa  agcatgtaaa   1680 caacatgtgt cacaagggat tttcatgacg cagccagcta cgactatcga agcattttca   1740
gatgaggaag tagagatccc agaggagaag gaaggagcag aggattcaaa aggaaatgga   1800
atagaggagc aagaggtaga agcaaatgag gaaaatgtga aggtgcatgg aggaagaaag   1860
gagaaaacag agatcctatc agatgaccctt acagacaaag cagaggtgag tgaaggcaag   1920
gcaaaatcag tgggagaagc agaggatggg cctgaaggta gagggatgg  aacctgtgag   1980 gaaggtagtt caggagcaga acactggcaa gatgaggaga gggagaaggg ggagaaagac   2040
aagggtagag gagaaatgga gaggccagga gagggagaga aggaactagc agagaaggaa   2100
gaatggaaga gagggatgg  ggaagagcag gagcaaaagg agaggagca  gggccatcag   2160 aaggaaagaa accaagagat ggaggaggga ggggaggagg agcatggaga aggagaagaa   2220
gaggagggag acagaagga  ggaagaagag aaggagggag aagggaaaga ggaaggagaa   2280
ggggaagaag tggagggaga acgtgaaaag gaggaaggag agaggaaaaa ggaggaaaga   2340
gcggggaagg aggagaaagg aggaggaagaa ggagaccaag gagaggggga gaggaggaa   2400 acagagggga gagggagga  aaaagaggag ggaggggaag tagagggagg ggaagtagag   2460
gaggggaaag gagagaggga agaggaagag gaggagggtg agggggaaga ggaggaaggg   2520 gaggggggaag aggaggaagg ggagggggaa gaggaggaag gagaagggaa agggggaggaa   2580 gaaggggaag aaggagaagg ggaggaagaa gggggaggaag gagaagggga gggggaagag   2640
gaggaaggag aaggggaggg agaagaggaa ggagaagggg agggagaaga ggaggaagga   2700
gaaggggagg gagaagagga aggagaaggg gagggagaag aggaggaagg agaagggaaa   2760
ggggaggagg aaggagagga aggagaaggg gaggggaaag aggagaagg  agaagggaaa   2820 ggggaggatg gagaaggga  ggggaagag  gaggaaggaa aatggaggg  ggaagaggag   2880 gaaggagaag gggagggga  agaggaagga gaagggaag  gggaggaagg agaaggggag   2940
```

-continued

| | |
|---|---|
| ggggaagagg aggaaggaga aggggagggg gaagaggagg aagggaaga agaagggag | 3000 |
| gaagaaggag agggagagga agaagggag ggagaagggg aggaagaaga ggaagggaa | 3060 |
| gtggaagggg aggtggaagg ggaggaagga gaggggaag gagaggaaga ggaaggagag | 3120 |
| gaggaaggag aagaaaggga aaaggagggg gaaggagaag aaaacaggag gaacagagaa | 3180 |
| gaggaggagg aagaagaggg gaagtatcag gagacaggcg aagaagagaa tgaaaggcag | 3240 |
| gatggagagg agtacaaaaa agtgagcaaa ataaaaggat ctgtgaaata tggcaaacat | 3300 |
| aaaacatatc aaaaaaagtc agttactaac acacagggaa atgggaaaga gcagaggtcc | 3360 |
| aaaatgccag tccagtcaaa acgactttta aaaaatgggc catcaggttc caaaaagttc | 3420 |
| tggaataata tattaccaca ttacttggaa ttgaagtaa | 3459 |

<210> SEQ ID NO 4
<211> LENGTH: 1152
<212> TYPE: PRT
<213> ORGANISM: Homo sapiens

<400> SEQUENCE: 4

```
Met Arg Glu Pro Glu Glu Leu Met Pro Asp Ser Gly Ala Val Phe Thr
1               5                   10                  15

Phe Gly Lys Ser Lys Phe Ala Glu Asn Asn Pro Gly Lys Phe Trp Phe
                20                  25                  30

Lys Asn Asp Val Pro Val His Leu Ser Cys Gly Asp Glu His Ser Ala
            35                  40                  45

Val Val Thr Gly Asn Asn Lys Leu Tyr Met Phe Gly Ser Asn Asn Trp
        50                  55                  60

Gly Gln Leu Gly Leu Gly Ser Lys Ser Ala Ile Ser Lys Pro Thr Cys
65                  70                  75                  80

Val Lys Ala Leu Lys Pro Glu Lys Val Lys Leu Ala Ala Cys Gly Arg
                85                  90                  95

Asn His Thr Leu Val Ser Thr Glu Gly Gly Asn Val Tyr Ala Thr Gly
            100                 105                 110

Gly Asn Asn Glu Gly Gln Leu Gly Leu Gly Asp Thr Glu Glu Arg Asn
        115                 120                 125

Thr Phe His Val Ile Ser Phe Phe Thr Ser Glu His Lys Ile Lys Gln
    130                 135                 140

Leu Ser Ala Gly Ser Asn Thr Ser Ala Ala Leu Thr Glu Asp Gly Arg
145                 150                 155                 160

Leu Phe Met Trp Gly Asp Asn Ser Glu Gly Gln Ile Gly Leu Lys Asn
                165                 170                 175

Val Ser Asn Val Cys Val Pro Gln Gln Val Thr Ile Gly Lys Pro Val
            180                 185                 190

Ser Trp Ile Ser Cys Gly Tyr Tyr His Ser Ala Phe Val Thr Thr Asp
        195                 200                 205

Gly Glu Leu Tyr Val Phe Gly Glu Pro Glu Asn Gly Lys Leu Gly Leu
    210                 215                 220

Pro Asn Gln Leu Leu Gly Asn His Arg Thr Pro Gln Leu Val Ser Glu
225                 230                 235                 240

Ile Pro Glu Lys Val Ile Gln Val Ala Cys Gly Gly Glu His Thr Val
                245                 250                 255

Val Leu Thr Glu Asn Ala Val Tyr Thr Phe Gly Leu Gly Gln Phe Gly
            260                 265                 270

Gln Leu Gly Leu Gly Thr Phe Leu Phe Glu Thr Ser Glu Pro Lys Val
        275                 280                 285
```

```
Ile Glu Asn Ile Arg Asp Gln Thr Ile Ser Tyr Ile Ser Cys Gly Glu
    290                 295                 300

Asn His Thr Ala Leu Ile Thr Asp Ile Gly Leu Met Tyr Thr Phe Gly
305                 310                 315                 320

Asp Gly Arg His Gly Lys Leu Gly Leu Gly Leu Glu Asn Phe Thr Asn
                325                 330                 335

His Phe Ile Pro Thr Leu Cys Ser Asn Phe Leu Arg Phe Ile Val Lys
            340                 345                 350

Leu Val Ala Cys Gly Gly Cys His Met Val Val Phe Ala Ala Pro His
        355                 360                 365

Arg Gly Val Ala Lys Glu Ile Glu Phe Asp Glu Ile Asn Asp Thr Cys
    370                 375                 380

Leu Ser Val Ala Thr Phe Leu Pro Tyr Ser Ser Leu Thr Ser Gly Asn
385                 390                 395                 400

Val Leu Gln Arg Thr Leu Ser Ala Arg Met Arg Arg Glu Arg Glu
                405                 410                 415

Arg Ser Pro Asp Ser Phe Ser Met Arg Arg Thr Leu Pro Pro Ile Glu
                420                 425                 430

Gly Thr Leu Gly Leu Ser Ala Cys Phe Leu Pro Asn Ser Val Phe Pro
            435                 440                 445

Arg Cys Ser Glu Arg Asn Leu Gln Glu Ser Val Leu Ser Glu Gln Asp
        450                 455                 460

Leu Met Gln Pro Glu Glu Pro Asp Tyr Leu Leu Asp Glu Met Thr Lys
465                 470                 475                 480

Glu Ala Glu Ile Asp Asn Ser Ser Thr Val Glu Ser Leu Gly Glu Thr
                485                 490                 495

Thr Asp Ile Leu Asn Met Thr His Ile Met Ser Leu Asn Ser Asn Glu
            500                 505                 510

Lys Ser Leu Lys Leu Ser Pro Val Gln Lys Gln Lys Gln Gln Thr
        515                 520                 525

Ile Gly Glu Leu Thr Gln Asp Thr Ala Leu Thr Glu Asn Asp Asp Ser
    530                 535                 540

Asp Glu Tyr Glu Glu Met Ser Glu Met Lys Glu Gly Lys Ala Cys Lys
545                 550                 555                 560

Gln His Val Ser Gln Gly Ile Phe Met Thr Gln Pro Ala Thr Thr Ile
                565                 570                 575

Glu Ala Phe Ser Asp Glu Glu Val Glu Ile Pro Glu Glu Lys Glu Gly
            580                 585                 590

Ala Glu Asp Ser Lys Gly Asn Gly Ile Glu Glu Gln Glu Val Glu Ala
        595                 600                 605

Asn Glu Glu Asn Val Lys Val His Gly Gly Arg Lys Gly Lys Thr Glu
    610                 615                 620

Ile Leu Ser Asp Asp Leu Thr Asp Lys Ala Glu Val Ser Glu Gly Lys
625                 630                 635                 640

Ala Lys Ser Val Gly Glu Ala Glu Asp Gly Pro Glu Gly Arg Gly Asp
                645                 650                 655

Gly Thr Cys Glu Glu Gly Ser Ser Gly Ala Glu His Trp Gln Asp Glu
            660                 665                 670

Glu Arg Glu Lys Gly Glu Lys Asp Lys Gly Arg Gly Glu Met Glu Arg
        675                 680                 685

Pro Gly Glu Gly Glu Lys Glu Leu Ala Glu Lys Glu Glu Trp Lys Lys
    690                 695                 700
```

-continued

```
Arg Asp Gly Glu Glu Gln Glu Gln Lys Glu Arg Gln Gly His Gln
705                 710                 715                 720

Lys Glu Arg Asn Gln Glu Met Glu Glu Gly Glu Glu His Gly
                725                 730                 735

Glu Gly Glu Glu Glu Gly Asp Arg Glu Glu Glu Glu Lys Glu
            740                 745                 750

Gly Glu Gly Lys Glu Glu Gly Glu Glu Val Glu Gly Glu Arg
        755                 760                 765

Glu Lys Glu Glu Gly Glu Arg Lys Lys Glu Glu Arg Ala Gly Lys Glu
    770                 775                 780

Glu Lys Gly Glu Glu Gly Asp Gln Gly Glu Gly Glu Glu Glu
785                 790                 795                 800

Thr Glu Gly Arg Gly Glu Glu Lys Glu Glu Gly Gly Glu Val Glu Gly
                805                 810                 815

Gly Glu Val Glu Glu Gly Lys Gly Glu Arg Glu Glu Glu Glu Glu
            820                 825                 830

Gly Glu Gly Glu Glu Glu Gly Glu Gly Glu Glu Glu Gly Glu
        835                 840                 845

Gly Glu Glu Glu Glu Gly Glu Gly Lys Gly Glu Glu Glu Gly Glu Glu
    850                 855                 860

Gly Glu Gly Glu Glu Gly Glu Gly Glu Gly Glu Gly Glu Glu
865                 870                 875                 880

Glu Glu Gly Glu Gly Glu Gly Glu Glu Gly Gly Glu Gly Glu
                885                 890                 895

Glu Glu Glu Gly Glu Gly Glu Gly Glu Glu Gly Glu Gly Glu Gly
            900                 905                 910

Glu Glu Glu Glu Gly Glu Gly Lys Gly Glu Glu Glu Gly Glu Gly
        915                 920                 925

Glu Gly Glu Gly Glu Gly Glu Gly Glu Gly Glu Gly Glu Asp Gly
    930                 935                 940

Glu Gly Glu Gly Glu Glu Glu Gly Glu Trp Glu Gly Glu Glu Glu
945                 950                 955                 960

Glu Gly Glu Gly Glu Gly Glu Glu Gly Glu Gly Glu Gly Glu Glu
                965                 970                 975

Gly Glu Gly Glu Gly Glu Glu Glu Gly Glu Gly Glu Gly Glu Glu
            980                 985                 990

Glu Glu Gly Glu Glu Glu Gly Glu Glu Gly Glu Gly Glu Glu
        995                 1000                1005

Gly Glu Gly Glu Gly Glu Glu Glu Glu Gly Glu Val Glu Gly Glu
    1010                1015                1020

Val Glu Gly Glu Glu Gly Glu Gly Glu Glu Glu Glu Gly Glu
1025                1030                1035                1040

Glu Glu Gly Glu Glu Arg Glu Lys Glu Gly Glu Gly Glu Glu Asn Arg
                1045                1050                1055

Arg Asn Arg Glu Glu Glu Glu Glu Glu Gly Lys Tyr Gln Glu Thr
            1060                1065                1070

Gly Glu Glu Glu Asn Glu Arg Gln Asp Gly Glu Glu Tyr Lys Lys Val
        1075                1080                1085

Ser Lys Ile Lys Gly Ser Val Lys Tyr Gly Lys His Lys Thr Tyr Gln
    1090                1095                1100

Lys Lys Ser Val Thr Asn Thr Gln Gly Asn Gly Lys Glu Gln Arg Ser
1105                1110                1115                1120

Lys Met Pro Val Gln Ser Lys Arg Leu Leu Lys Asn Gly Pro Ser Gly
```

-continued

```
                1125                1130                1135
Ser Lys Lys Phe Trp Asn Asn Ile Leu Pro His Tyr Leu Glu Leu Lys
            1140                1145                1150

<210> SEQ ID NO 5
<211> LENGTH: 199
<212> TYPE: DNA
<213> ORGANISM: Homo sapiens

<400> SEQUENCE: 5
gggccccaga agcctggtgg ttgtttgtcc ttctcagggg aaaagtgagg cggccccttg      60
gaggaagggg ccgggcagaa tgatctaatc ggattccaag cagctcaggg gattgtcttt     120
ttctagcacc ttcttgccac tcctaagcgt cctccgtgac cccggctggg atttagcctg     180
gtgctgtgtc agccccggt                                                  199
```

RPGR GENE THERAPY FOR RETINITIS PIGMENTOSA

CROSS-REFERENCE TO RELATED APPLICATIONS

This application is a continuation of U.S. application Ser. No. 15/328,617 filed Jan. 24, 2017, which is a 371 of PCT/US2015/040866, filed Jul. 17, 2015 and which claims the benefit of priority under 35 USC § 119(e) to U.S. Patent Application Ser. No. 62/028,638, filed on Jul. 24, 2014. The entire contents of the foregoing applications are incorporated by reference in their entireties.

FEDERALLY SPONSORED RESEARCH OR DEVELOPMENT

This invention was made with Government support under Grant Nos. EY10581 and 5P30EY14104 awarded by the National Institutes of Health. The Government has certain rights in the invention.

TECHNICAL FIELD

The invention relates to methods for treating a human subject who has X-linked Retinitis Pigmentosa (XLRP) or another ophthalmological condition due to a loss-of-function mutation in the gene encoding the retinitis pigmentosa GTPase regulator (RPGR) protein, the method comprising administering to the subject a nucleic acid comprising an adeno-associated viral vector comprising an abbreviated human RPGR cDNA.

BACKGROUND

Retinitis pigmentosa (RP) is a leading form of inherited blindness in humans. Of the three general modes of inheritance (autosomal dominant, autosomal recessive, and X-linked), X-linked RP (XLRP) is associated with a severe form of disease involving both rod and cone photoreceptors as primary targets (Berson 1993; Sandberg and others 2007). Over 70% of X-linked RP and 10%-20% of all RP cases are caused by mutations in the gene encoding RPGR (Bader and others 2003; Branham and others 2012; Churchill and others; Pelletier and others 2007). Given that mutations in well over 100 genes are currently known to cause RP and the greater severity of X-linked disease, RPGR is one of the most important RP disease genes.

SUMMARY

The present invention is based on the discovery of an abbreviated form of human RPGR that successfully recreates functional RPGR activity, and thus includes methods for treating subjects who have RP caused by mutations in RPGR. Subjects who can be treated by the present methods can include those who have loss of visual function (e.g., impaired response on electroretinographic (ERG) testing), but retain some photoreceptor cells as determined by optical coherence tomography (OCT).

Thus, in one aspect, the invention provides methods for treating a human subject who has XLRP or another clinically-defined ophthalmological condition due to a loss-of-function mutation in the gene encoding the retinitis pigmentosa GTPase regulator (RPGR) protein. The methods include administering to the subject a nucleic acid comprising an adeno-associated viral vector comprising an abbreviated human RPGR cDNA, wherein the abbreviated human RPGR cDNA encodes a protein that is at least 80% identical to the full length of SEQ ID NO:2, optionally with a deletion of up to a total of 200 additional amino acids in the region surrounding the deleted region in SEQ ID NO:2 (i.e., between amino acids 861 and 862 of SEQ ID NO:2).

In some embodiments, the RPGR cDNA is under the control of a human rhodopsin kinase (hRK) promoter, e.g., an hRK promoter that comprises or consists essentially SEQ ID NO:5.

In some embodiments, the adeno-associated viral vector is AAV-2, serotype-8 (AAV2/8) or AAV-8.

In some embodiments, the RPGR cDNA comprises or consists essentially of a sequence that is at least 80% identical to SEQ ID NO:1.

In some embodiments, the human RPGR cDNA encodes a protein that is at least 95% identical to the full length of SEQ ID NO:2.

In some embodiments, the methods include administering the nucleic acid in a low dose of about $2 \times 10^{10}$ vg/mL, a middle dose of about $2 \times 10^{11}$ vg/mL, or a high dose of about $2 \times 10^{12}$ vg/mL. In some embodiments, the nucleic acid is administered into the subretinal space. In some embodiments, a micro injection cannula is inserted into the subretinal space, temporal to the optic nerve and just above the major arcade vessels, so that fluid flow can be directed towards the macula.

In another aspect, the invention provides nucleic acids encoding an abbreviated human RPGR, wherein the abbreviated human RPGR cDNA encodes a protein that is at least 80% identical to the full length of SEQ ID NO:2, optionally with a deletion of up to 200 additional amino acids surrounding the deleted region of SEQ ID NO:2.

In some embodiments, the RPGR cDNA is under the control of a human rhodopsin kinase (hRK) promoter, e.g., an hRK promoter that comprises or consists essentially SEQ ID NO:5.

In some embodiments, the RPGR cDNA comprises or consists essentially of a sequence that is at least 80% identical to SEQ ID NO:1.

In some embodiments, the human RPGR cDNA encodes a protein that is at least 95% identical to the full length of SEQ ID NO:2.

In some embodiments, the human RPGR cDNA is at least 80% identical to the full length of SEQ ID NO:1, optionally with a deletion of nucleotides encoding up to 200 additional amino acids surrounding the deleted region.

Also provided herein are vectors, e.g., adeno-associated viral vectors, e.g., AAV-2, serotype-8 (AAV2/8) or AAV-8, comprising the nucleic acids encoding an abbreviated human RPGR as described herein, as well as isolated cells (i.e., cells that are not present in a living human subject or host animal) that harbor the nucleic acids encoding an abbreviated human RPGR and optionally express the abbreviated human RPGR protein.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

(FIG. 1A) Maps of the native human RPGR ORF15 coding region and both shortened forms of AAV-delivered human ORF15cDNA. (FIG. 1B) Immunoblots for the two recombinant forms of human RPGR-ORF15. AAV delivery of the small-deletion human cDNA (AAV-ORF15-L, "long form") leads to expression of a human RPGR-ORF15 protein of ~160 kD in size. AAV delivery of the large-deletion human cDNA (AAV-ORF15-S, "short form") leads to expression of a protein of ~130 kD in size. Both forms of human RPGR-ORF15 protein are smaller than endogenous human RPGR ORF15 found in human retinal tissue (~200 kD).

FIGS. 2A-2D. RPGR ORF15 expression in RPGR$^{-/-}$ mouse retinas following subretinal delivery of AAV-RPGR ORF15. (FIG. 2A) Fluorescence images of both the short (ORF15-S) and long (ORF15-L) forms of human RPGR ORF15 protein expression superimposed on Nomarski images to illustrate the layers of the outer retina. Staining of unfixed frozen retinal sections was performed at 3 weeks following treatment at 1-2 months of age. (FIG. 2B) Fluorescence images of both forms of human RPGR ORF15 co-localized with rootletin. Similar to WT, both forms of human RPGR ORF15 correctly localized to the photoreceptor connecting cilium just distal to rootletin. RPE, retinal pigment epithelium; OS, outer segment; CC (TZ), connecting cilium (transition zone); IS, inner segment; ONL, outer nuclear layer. (FIG. 2C) Ratio of hRPGR fluorescent particles to fluorescent rootletin fibers at the connecting cilium for Rpgr$^{-/-}$ eyes (n=3) treated with ORF15-S, Rpgr$^{-/-}$ eyes (n=3) treated with ORF15-L, and wt eyes (n=3). Counts were obtained for both rootletin within the inner segment and RPGR just distal to rootletin over a 100 µm length of midperipheral retina. Values are means±1 standard error. (FIG. 2D) Expression pattern of short and long form ORF15 protein in fixed floating retinal sections of Rpgr$^{-/-}$ mice. Sections were stained for human RPGR ORF15 protein localization 4-6 weeks following treatment at 2-3 months of age. In wt retina, murine RPGR ORF15 protein was seen as a discrete green fluorescent signal (dots) occupying the region between the photoreceptor inner and outer segments, at the level of the transition zone or connecting cilium. In contrast, the fluorescent signal for the short form of ORF15 (AAV-ORF15-S) is not limited to level of the photoreceptor connecting cilium but is also seen as diffuse signal throughout the inner and outer segments as well. The fluorescent signal for the long form of ORF15 shows very little, if any mislocalization, and is largely limited to the connecting cilium region similar to wt. OS, outer segment; CC (TZ), connecting cilium (transition zone); IS, inner segment; ONL, outer nuclear layer.

(FIG. 4A) Shown are stacked bar graphs for ONL thickness (top) and IS/OS length (bottom) for treated (red in original) and fellow control (blue in original) eyes in 3 mice at 18 months of age. (FIG. 4B) Representative light micrographs from a WT mouse and an ORF15-l treated and fellow control eye from an RPGR-/- mouse at 18 months of age. Images were taken from the mid periphery along the vertical meridian in the superior retina, FIGS. 5A-5C. (FIG. 5A) Rod a-wave, rod b-wave, and cone b-wave amplitudes from 16 RPGR-/- mice at 11-14 months of age. Control eyes (OD) showed disproportionate loss of cone b-wave amplitude relative to rod b-wave amplitude compared with the lower limits for wild-type mice. Except in one instance, treated eyes (OS) all had larger responses than fellow control eyes In particular, note that more than half of the treated eyes at this age had rod ERG b-wave amplitudes that were at or above the lower limit of wild-type. Mean values for all three measures were significantly different between eyes (P<0.01).

DETAILED DESCRIPTION

Figure 1A:
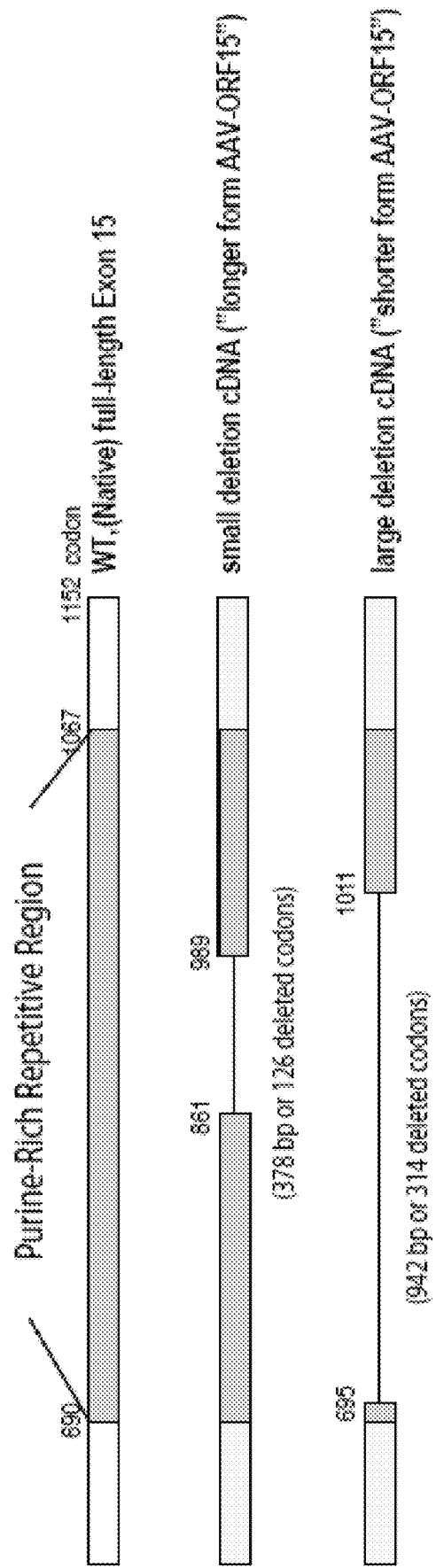
FIGS. 1A-1B.

Viral vector-mediated somatic gene therapy has shown great promise in treating animal models of human retinal degenerative disease. To date, there have been a number of successful studies using adeno-associated virus (AAV)-mediated gene delivery to rescue photoreceptor degeneration in small animal models (Ali and others 2000; Pang and others 2012; Pawlyk and others 2010; Pawlyk and others 2005; Tan and others 2009) and large animal models (Acland and others 2001; Alexander and others 2007; Beltran and others 2012; Komaromy and others 2010; Lheriteau and others 2009). In these cases, the retinal pigment epithelium (RPE) or photoreceptors have been the primary targets for transgene expression. In addition, phase I clinical trials involving gene therapy for patients with Leber Congenital Amaurosis (LCA) targeting the RPE (Bainbridge and others 2008; Cideciyan and others 2008; Maguire and others 2008) and more recently choroideremia (Maclaren and others 2014), have already met with some success. There are currently no clinical trials using AAV-mediated gene replacement therapy for the treatment of patients with X-linked RP.

The present inventors have previously demonstrated functional and morphological rescue of both rod and cone photoreceptor cells in mice lacking RPGR using an abbreviated murine RPGR ORF15 isoform lacking about 600 bp in the purine-rich carboxyl terminus using a transgenic approach (Hong and others 2005). Some variation in the length of the repetitive region is frequently found in normal individuals (Bader and others 2003; Jacobi and others 2005; Karra and others 2006). However, the function of an abbreviated human RPGR has not been described.

In the present study, a shortened human RPGR ORF15 replacement gene, driven by a previously described rhodopsin kinase (RK) promoter (Khani and others 2007; Sun and others 2010) and delivered in the fast acting AAV8 vector (Allocca and others 2007; Natkunarajah and others 2008), was able to rescue the photoreceptor degeneration phenotype in the RPGR knockout mouse model. The purine-rich repetitive region of ORF15 exon is required for correct subcellular localization and function of RPGR, but that shortening of its length by up to one third appears not to compromise its function. This shortened RPGR replacement gene offers a viable alternative to the so far evasive "full-length" RPGR ORF15 in future human gene therapy trials.

RPGR

RPGR is expressed in a complex pattern, with both default and ORF15 variants having been described (Vervoort and others 2000). The default or constitutive form of RPGR spans exons 1-19 and ORF15 terminates in a large alternative exon designated ORF15 before the onset of exons 16-19. The ORF15 exon is unique in that it contains a long stretch of purine rich repetitive sequence that proved difficult to clone into cDNA and unstable in many procedures of recombinant DNA manipulations. While the smaller default form of RPGR is the predominant form in tissues with motile cilia (Hong et al., 2003) and many types of primary cilia (our unpublished data), the ORF15 isoform of RPGR is necessary for normal rod and cone function in the retina (Vervoort and others 2000; Vervoort and Wright 2002) and is expressed primarily in photoreceptors (Hong and others 2003). ORF15 is also a common site for mutations in RPGR, with mutations identified in 22-60% of patients with X-linked RP (Breuer and others 2002; Vervoort and others 2000).

The present inventors contributed to the development of the first mouse model of X-linked RP carrying a null mutation in RPGR with no detectable levels of any isoforms of RPGR (Hong and others 2000). RPGR null mice manifest a slowly progressive retinal degeneration that is characterized by early cone opsin mislocalization in cell bodies and synapses and reduced levels of rhodopsin in rods. As a result, these mice have a cone-rod degeneration. By 12 months of age significant photoreceptor cell loss and decline in cone and rod function, as measured by electroretinograms (ERG), become apparent. In the retina, RPGR is bound to the photoreceptor connecting cilium located in between the inner and outer segments via an RPGR interacting protein (RPGRIP1) (see, e.g., Boylan and Wright 2000; Hong and others 2001; Roepman and others 2000). The connecting cilium is analogous to the transition zone of motile or primary cilia that may serve as a gateway to the outer segment. This subcellular localization pattern and the mutant mouse phenotype suggest that RPGR may have a role in protein trafficking between the inner and outer segment of both rods and cones (Hong and Li 2002; Hong and others 2000; Hong and others 2001). In attempts to develop an RPGR mutant mouse model with a faster course of degeneration, several other RPGR mouse lines have been recently developed (Brunner, et al, 2010; Huang et al, 2012). There has also been a recent report of a naturally occurring model (rd9) of X-linked RPGR (Thompson and others 2012). In all of these cases, including the RPGR null mice display a slowly progressive loss photoreceptors but with varying degree of rod and cone involvement which may be due, in part, to differences in strain and/or pigmentation. These findings indicate that the slow rate of degeneration in the knockout model is due to species differences rather than the ablation being incomplete, and confirm the applicability of this murine model in therapeutic studies of null RPGR mutations in patients.

Two variants (A and C) of the full-length human RPGR (also known as CRD; RP3; COD1; PCDX; RP15; XLRP3; orf15; and CORDX1) are described in GenBank; Isoform A is at Accession No. NM_000328.2 (nucleic acid) and NP_000319.1 (protein); Isoform C is at Accession No. NM_001034853.1 (nucleic acid) and NP_001030025.1 (protein). Variant (A) uses an alternate splice site and contains multiple alternative exons in the 3' coding region, compared to variant C, and encodes isoform A (also referred to as isoform 1) that is shorter and has a distinct C-terminus, compared to isoform C. The sequence used in the exemplary compositions described herein is set forth below as SEQ ID NO:1. The sequences of human RPGR useful in the compositions and methods described herein can be at least 80%, e.g., 85%, 90%, 95%, or 100% identical to the full length of SEQ ID NO:1, with up to an additional 50, 100, 150, or 200 amino acids deleted from the deleted region, indicated by dashes in the sequence below.

```
Abbreviated form of Human RPGRORF15 sequence with 378bp deleted, and
deleted region shown by dashes ("-"; number of dashes does not
correlate with size of deletion)
                                                              (SEQ ID NO: 1)
ATGAGGGAGCCGGAAGAGCTGATGCCCGATTCGGGTGCTGTGTTTACATTTGGGAAAAGTAAATTTGCT

GAAAATAATCCCGGTAAATTCTGGTTTAAAAATGATGTCCCTGTACATCTTTCATGTGGAGATGAACAT

TCTGCTGTTGTTACCGGAAATAATAAACTTTACATGTTTGGCAGTAACAACTGGGGTCAGTTAGGATTA

GGATCAAAGTCAGCCATCAGCAAGCCAACATGTGTCAAAGCTCTAAAACCTGAAAAAGTGAAATTAGCT
```

-continued

```
GCCTGTGGAAGGAACCACACCCTGGTGTCAACAGAAGGAGGCAATGTATATGCAACTGGTGGAAATAAT
GAAGGACAGTTGGGGCTTGGTGACACCGAAGAAAGAAACACTTTTCATGTAATTAGCTTTTTTACATCC
GAGCATAAGATTAAGCAGCTGTCTGCTGGATCTAATACTTCAGCTGCCCTAACTGAGGATGGAAGACTT
TTTATGTGGGGTGACAATTCCGAAGGGCAAATTGGTTTAAAAAATGTAAGTAATGTCTGTGTCCCTCAG
CAAGTGACCATTGGGAAACCTGTCTCCTGGATCTCTTGTGGATATTACCATTCAGCTTTTGTAACAACA
GATGGTGAGCTATATGTGTTTGGAGAACCTGAGAATGGGAAGTTAGGTCTTCCCAATCAGCTCCTGGGC
AATCACAGAACACCCCAGCTGGTGTCTGAAATTCCGGAGAAGGTGATCCAAGTAGCCTGTGGTGGAGAG
CATACTGTGGTTCTCACGGAGAATGCTGTGTATACCTTTGGGCTGGGACAATTTGGTCAGCTGGGTCTT
GGCACTTTTCTTTTTGAAACTTCAGAACCCAAAGTCATTGAGAATATTAGGGATCAAACAATAAGTTAT
ATTTCTTGTGGAGAAAATCACACAGCTTTGATAACAGATATCGGCCTTATGTATACTTTTGGAGATGGT
CGCCACGGAAAATTAGGACTTGGACTGGAGAATTTTACCAATCACTTCATTCCTACTTTGTGCTCTAAT
TTTTTGAGGTTTATAGTTAAATTGGTTGCTTGTGGTGGATGTCACATGGTAGTTTTTGCTGCTCCTCAT
CGTGGTGTGGCAAAAGAAATTGAATTCGATGAAATAAATGATACTTGCTTATCTGTGGCGACTTTTCTG
CCGTATAGCAGTTTAACCTCAGGAAATGTACTGCAGAGGACTCTATCAGCACGTATGCGGCGAAGAGAG
AGGGAGAGGTCTCCAGATTCTTTTTCAATGAGGAGAACACTACCTCCAATAGAAGGGACTCTTGGCCTT
TCTGCTTGTTTTCTCCCCAATTCAGTCTTTCCACGATGTTCTGAGAGAAACCTCCAAGAGAGTGTCTTA
TCTGAACAGGACCTCATGCAGCCAGAGGAACCAGATTATTTGCTAGATGAAATGACCAAAGAAGCAGAG
ATAGATAATTCTTCAACTGTAGAAAGCCTTGGAGAAACTACTGATATCTTAAACATGACACACATCATG
AGCCTGAATTCCAATGAAAAGTCATTAAAATTATCACCAGTTCAGAAACAAAAGAAACAACAAACAATT
GGGGAACTGACGCAGGATACAGCTCTTACTGAAAACGATGATAGTGATGAATATGAAGAAATGTCAGAA
ATGAAAGAAGGGAAAGCATGTAAACAACATGTGTCACAAGGGATTTTCATGACGCAGCCAGCTACGACT
ATCGAAGCATTTTCAGATGAGGAAGTAGAGATCCCAGAGGAGAAGGAAGGAGCAGAGGATTCAAAAGGA
AATGGAATAGAGGAGCAAGAGGTAGAAGCAAATGAGGAAAATGTGAAGGTGCATGGAGGAAGAAAGGAG
AAAACAGAGATCCTATCAGATGACCTTACAGACAAAGCAGAGGTGAGTGAAGGCAAGGCAAAATCAGTG
GGAGAAGCAGAGGATGGGCCTGAAGGTAGAGGGGATGGAACCTGTGAGGAAGGTAGTTCAGGAGCAGAA
CACTGGCAAGATGAGGAGAGGGAGAAGGGGGAGAAAGACAAGGGTAGAGGAGAAATGGAGAGGCCAGGA
GAGGGAGAGAAGGAACTAGCAGAGAAGGAAGAATGGAAGAAGAGGGATGGGGAAGAGCAGGAGCAAAAG
GAGAGGGAGCAGGGCCATCAGAAGGAAAGAAACCAAGAGATGGAGGAGGGAGGGGAGGAGGAGCATGGA
GAAGGAGAAGAAGAGGAGGGAGACAGAGAAGAGGAAGAAGAGAAGGAGGGAGAAGGGAAAGAGGAAGGA
GAAGGGGAAGAAGTGGAGGGAGAACGTGAAAAGGAGGAAGGAGAGAGGAAAAAGGAGGAAAGAGCGGGG
AAGGAGGAGAAAGGAGAGGAAGAAGGAGACCAAGGAGAGGGGAAGAGGAGGAAACAGAGGGGAGAGGG
GAGGAAAAAGAGGAGGGAGGGGAAGTAGAGGGAGGGGAAGTAGAGGAGGGGAAAGGAGAGAGGGAAGAG
GAAGAGGAGGAGGGTGAGGGGAAGAGGAGGAAGGGAGGGGAAGAGGAGGAAGGGAGGGGGAAGAG
GAGGAAGGAGAAGGGAAAGGGAGGAAGAA-GGGGAGGGGAAGAGGAGGAAGGGGAAGAAGAAGGGGA
GGAAGAAGGAGAGGGAGAGGAAGAAGGGGAGGGAGAAGGGGAGGAAGAAGAGGAAGGGGAAGTGGAAGG
GGAGGTGGAAGGGGAGGAAGGAGAGGGGGAAGGAGAGGAAGAGGAAGGAGAGGAGGAAGGAGAAGAAAG
GGAAAAGGAGGGGGAAGGAGAAGAAAACAGGAGGAACAGAGAAGAGGAGGAGGAAGAAGAGGGGAAGTA
TCAGGAGACAGGCGAAGAAGAGAATGAAAGGCAGGATGGAGAGGAGTACAAAAAAGTGAGCAAAATAAA
AGGATCTGTGAAATATGGCAAACATAAAACATATCAAAAAAAGTCAGTTACTAACACACAGGGAAATGG
```

```
GAAAGAGCAGAGGTCCAAAATGCCAGTCCAGTCAAAACGACTTTTAAAAAATGGGCCATCAGGTTCCAA

AAAGTTCTGGAATAATATATTACCACATTACTTGGAATTGAAGTAA
```

Protein sequence for abbreviated form of Human RPGRORF15 with deleted region shown by dashes ("-"; number of dashes does not correlate with size of deletion)

```
atgagggagccggaagagctgatgcccgattcgggtgctgtgtttacatttgggaaaagt
 M   R   E   P   E   E   L   M   P   D   S   G   A   V   F   T   F   G   K   S aaatttgctgaaaataatcccggtaaattctggtttaaaaatgatgtccctgtacatctt
 K   F   A   E   N   N   P   G   K   F   W   F   K   N   D   V   P   V   H   L tcatgtggagatgaacattctgctgttgttaccggaaataataaactttacatgtttggc
 S   C   G   D   E   H   S   A   V   V   T   G   N   N   K   L   Y   M   F   G agtaacaactggggtcagttaggattaggatcaaagtcagccatcagcaagccaacatgt
 S   N   N   W   G   Q   L   G   L   G   S   K   S   A   I   S   K   P   T   C gtcaaagctctaaaacctgaaaaagtgaaattagctgcctgtggaaggaaccacaccctg
 V   K   A   L   K   P   E   K   V   K   L   A   A   C   G   R   N   H   T   L gtgtcaacagaaggaggcaatgtatatgcaactggtggaaataatgaaggacagttgggg
 V   S   T   E   G   G   N   V   Y   A   T   G   G   N   N   E   G   Q   L   G cttggtgacaccgaagaaagaaacacttttcatgtaattagcttttttacatccgagcat
 L   G   D   T   E   E   R   N   T   F   H   V   I   S   F   F   T   S   E   H aagattaagcagctgtctgctggatctaatacttcagctgccctaactgaggatggaaga
 K   I   K   Q   L   S   A   G   S   N   T   S   A   A   L   T   E   D   G   R cttttatgtggggtgacaattccgaagggcaaattggtttaaaaaatgtaagtaatgtc
 L   F   M   W   G   D   N   S   E   G   Q   I   G   L   K   N   V   S   N   V tgtgtccctcagcaagtgaccattgggaaacctgtctcctggatctcttgtggatattac
 C   V   P   Q   Q   V   T   I   G   K   P   V   S   W   I   S   C   G   Y   Y cattcagcttttgtaacaacagatggtgagctatatgtgtttggagaacctgagaatggg
 H   S   A   F   V   T   T   D   G   E   L   Y   V   F   G   E   P   E   N   G aagttaggtcttcccaatcagctcctgggcaatcacagaacaccccagctggtgtctgaa
 K   L   G   L   P   N   Q   L   L   G   N   H   R   T   P   Q   L   V   S   E attccggagaaggtgatccaagtagcctgtggtggagagcatactgtggttctcacggag
 I   P   E   K   V   I   Q   V   A   C   G   G   E   H   T   V   V   L   T   E aatgctgtgtataccttttgggctgggacaattttggtcagctgggtcttggcacttttctt
 N   A   V   Y   T   F   G   L   G   Q   F   G   Q   L   G   L   G   T   F   L tttgaaacttcagaacccaaagtcattgagaatattagggatcaaacaataagttatatt
 F   E   T   S   E   P   K   V   I   E   N   I   R   D   Q   T   I   S   Y   I tcttgtggagaaaatcacacagctttgataacagatatcggcctttatgtatacttttgga
 S   C   G   E   N   H   T   A   L   I   T   D   I   G   L   M   Y   T   F   G gatggtcgccacggaaaattaggacttggactggagaattttaccaatcacttcattcct
 D   G   R   H   G   K   L   G   L   G   L   E   N   F   T   N   H   F   I   P actttgtgctctaatttttgaggtttatagttaaattggttgcttgtggtggatgtcac
 T   L   C   S   N   F   L   R   F   I   V   K   L   V   A   C   G   G   C   H atggtagttttgctgctcctcatcgtggtgtggcaaaagaaattgaattcgatgaaata
 M   V   V   F   A   A   P   H   R   G   V   A   K   E   I   E   F   D   E   I aatgatacttgcttatctgtggcgacttttctgccgtatagcagtttaacctcaggaaat
 N   D   T   C   L   S   V   A   T   F   L   P   Y   S   S   L   T   S   G   N gtactgcagaggactctatcagcacgtatgcggcgaagagagagggagaggtctccagat
 V   L   Q   R   T   L   S   A   R   M   R   R   R   E   R   E   R   S   P   D tcttttttcaatgaggagaacactacctccaatagaagggactcttggcctttctgcttgt
 S   F   S   M   R   R   T   L   P   P   I   E   G   T   L   G   L   S   A   C tttctccccaattcagtctttccacgatgttctgagagaaacctccaagagagtgtctta
 F   L   P   N   S   V   F   P   R   C   S   E   R   N   L   Q   E   S   V   L tctgaacaggacctcatgcagccagaggaaccagattatttgctagatgaaatgaccaaa
 S   E   Q   D   L   M   Q   P   E   E   P   D   Y   L   L   D   E   M   T   K
```

```
gaagcagagatagataattcttcaactgtagaaagccttggagaaactactgatatctta
 E  A  E  I  D  N  S  S  T  V  E  S  L  G  E  T  T  D  I  L aacatgacacacatcatgagcctgaattccaatgaaaagtcattaaaattatcaccagtt
 N  M  T  H  I  M  S  L  N  S  N  E  K  S  L  K  L  S  P  V cagaaacaaaagaaacaacaaacaattggggaactgacgcaggatacagctcttactgaa
 Q  K  Q  K  K  Q  Q  T  I  G  E  L  T  Q  D  T  A  L  T  E aacgatgatagtgatgaatatgaagaaatgtcagaaatgaaagaagggaaagcatgtaaa
 N  D  D  S  D  E  Y  E  E  M  S  E  M  K  E  G  K  A  C  K caacatgtgtcacaagggattttcatgacgcagccagctacgactatcgaagcattttca
 Q  H  V  S  Q  G  I  F  M  T  Q  P  A  T  T  I  E  A  F  S gatgaggaagtagagatcccagaggagaaggaaggagcagaggattcaaaaggaaatgga
 D  E  E  V  E  I  P  E  E  K  E  G  A  E  D  S  K  G  N  G atagaggagcaagaggtagaagcaaatgaggaaaatgtgaaggtgcatggaggaagaaag
 I  E  E  Q  E  V  E  A  N  E  E  N  V  K  V  H  G  G  R  K gagaaaacagagatcctatcagatgacctt acagacaaagcagaggtgagtgaaggcaag
 E  K  T  E  I  L  S  D  D  L  T  D  K  A  E  V  S  E  G  K gcaaaatcagtgggagaagcagaggatgggcctgaaggtagaggggatggaacctgtgag
 A  K  S  V  G  E  A  E  D  G  P  E  G  R  G  D  G  T  C  E gaaggtagttcaggagcagaacactggcaagatgaggagagggagaaggggagaaagac
 E  G  S  S  G  A  E  H  W  Q  D  E  E  R  E  K  G  E  K  D aagggtagaggagaaatggagaggccaggagagggagagaaggaactagcagagaaggaa
 K  G  R  G  E  M  E  R  P  G  E  G  E  K  E  L  A  E  K  E gaatggaagaagagggatggggaagagcaggagcaaaaggagagggagcagggccatcag
 E  W  K  K  R  D  G  E  E  Q  E  Q  K  E  R  E  Q  G  H  Q aaggaaagaaaccaagagatggaggagggaggggaggaggagcatggagaaggagaagaa
 K  E  R  N  Q  E  M  E  E  G  G  E  E  E  H  G  E  G  E  E gaggagggagacagagaagaggaagaagaagaaggagggagaagggaaagaggaaggagaa
 E  E  G  D  R  E  E  E  E  K  E  G  E  G  K  E  E  G  E ggggaagaagtggagggagaacgtgaaaaggaggaaggagagaggaaaaaggaggaaaga
 G  E  E  V  E  G  E  R  E  K  E  E  G  E  R  K  K  E  E  R gcggggaaggaggagaaaggagaggaagaaggagaccaaggagaggggaagaggaggaa
 A  G  K  E  E  K  G  E  E  E  G  D  Q  G  E  G  E  E  E  E acagaggggagaggggaggaaaaagaggagggagggggaagtagagggagggaagtagag
 T  E  G  R  G  E  E  K  E  E  G  G  E  V  E  G  G  E  V  E gaggggaaaggagagagggaagaggaagaggaggagggtgagggggaagaggaggaaggg
 E  G  K  G  E  R  E  E  E  E  E  G  E  G  E  E  E  E  G gaggggaagaggaggaagggagggggaagaggaggaaggagaagggaaagggaggaa
 E  G  E  E  E  E  G  E  G  E  E  E  E  G  E  G  K  G  E  E gaa------------------ggggagggggaagaggaggaaggggaagaagaaggggag
 E  -  -  -  -  -  -  -  -  -  -  -  -  -  -  -  -  -  G  E  G  E  E  E  E  G  E  E  E  G  E gaagaaggagggagaggaagaagggagggagaagggaggaagaagaggaagggaa
 E  E  G  E  E  E  G  E  G  E  G  E  E  E  E  G  E gtggaagggaggtggaagggaggaaggagaggggaaggagaggaagaggaaggagag
 V  E  G  E  V  E  G  E  E  G  E  G  E  G  E  E  E  E  G  E gaggaaggagaagaaagggaaaaggaggggaaggagaagaaaacaggaggaacagagaa
 E  E  G  E  E  R  E  K  E  G  E  G  E  E  N  R  R  N  R  E gaggaggaggaagaagaggggaagtatcaggagacaggcgaagaagaatgaaaggcag
 E  E  E  E  E  G  K  Y  Q  E  T  G  E  E  E  N  E  R  Q gatggagaggagtacaaaaaagtgagcaaaataaaaggatctgtgaaatatggcaaacat
 D  G  E  E  Y  K  K  V  S  K  I  K  G  S  V  K  Y  G  K  H aaaacatatcaaaaaaagtcagttactaacacacagggaaatgggaaagagcagaggtcc
 K  T  Y  Q  K  K  S  V  T  N  T  Q  G  N  G  K  E  Q  R  S aaaatgccagtccagtcaaaacgacttttaaaaaatgggccatcaggttccaaaaagttc
 K  M  P  V  Q  S  K  R  L  L  K  N  G  P  S  G  S  K  K  F
``` tggaataatatattaccacattacttggaattgaagtaa (SEQ ID NO: 1)
 W  N  N  I  L  P  H  Y  L  E  L  K  - (SEQ ID NO:2)

Full-Length Human RPGRORF15 cDNA sequence; 378bp deleted in
Abbreviated form are bolded and underlined in sequence below (SEQ ID NO:3)
ATGAGGGAGCCGGAAGAGCTGATGCCCGATTCGGGTGCTGTGTTTACATTTGGGAAAAGTAAATTTGCT

GAAAATAATCCCGGTAAATTCTGGTTTAAAAATGATGTCCCTGTACATCTTTCATGTGGAGATGAACAT

TCTGCTGTTGTTACCGGAAATAATAAACTTTACATGTTTGGCAGTAACAACTGGGGTCAGTTAGGATTA

GGATCAAAGTCAGCCATCAGCAAGCCAACATGTGTCAAAGCTCTAAAACCTGAAAAAGTGAAATTAGCT

GCCTGTGGAAGGAACCACACCCTGGTGTCAACAGAAGGAGGCAATGTATATGCAACTGGTGGAAATAAT

GAAGGACAGTTGGGGCTTGGTGACACCGAAGAAGAAACACTTTTCATGTAATTAGCTTTTTTACATCC

GAGCATAAGATTAAGCAGCTGTCTGCTGGATCTAATACTTCAGCTGCCCTAACTGAGGATGGAAGACTT

TTTATGTGGGGTGACAATTCCGAAGGGCAAATTGGTTTAAAAAATGTAAGTAATGTCTGTGTCCCTCAG

CAAGTGACCATTGGGAAACCTGTCTCCTGGATCTCTTGTGGATATTACCATTCAGCTTTTGTAACAACA

GATGGTGAGCTATATGTGTTTGGAGAACCTGAGAATGGGAAGTTAGGTCTTCCCAATCAGCTCCTGGGC

AATCACAGAACACCCCAGCTGGTGTCTGAAATTCCGGAGAAGGTGATCCAAGTAGCCTGTGGTGGAGAG

CATACTGTGGTTCTCACGGAGAATGCTGTGTATACCTTTGGGCTGGGACAATTTGGTCAGCTGGGTCTT

GGCACTTTTCTTTTTGAAACTTCAGAACCCAAAGTCATTGAGAATATTAGGGATCAAACAATAAGTTAT

ATTTCTTGTGGAGAAAATCACACAGCTTTGATAACAGATATCGGCCTTATGTATACTTTTGGAGATGGT

CGCCACGGAAAATTAGGACTTGGACTGGAGAATTTTACCAATCACTTCATTCCTACTTTGTGCTCTAAT

TTTTTGAGGTTTATAGTTAAATTGGTTGCTTGTGGTGGATGTCACATGGTAGTTTTTGCTGCTCCTCAT

CGTGGTGTGGCAAAAGAAATTGAATTCGATGAAATAAATGATACTTGCTTATCTGTGGCGACTTTTCTG

CCGTATAGCAGTTTAACCTCAGGAAATGTACTGCAGAGGACTCTATCAGCACGTATGCGGCGAAGAGAG

AGGGAGAGGTCTCCAGATTCTTTTTCAATGAGGAGAACACTACCTCCAATAGAAGGGACTCTTGGCCTT

TCTGCTTGTTTTCTCCCCAATTCAGTCTTTCCACGATGTTCTGAGAGAAACCTCCAAGAGAGTGTCTTA

TCTGAACAGGACCTCATGCAGCCAGAGGAACCAGATTATTTGCTAGATGAAATGACCAAAGAAGCAGAG

ATAGATAATTCTTCAACTGTAGAAAGCCTTGGAGAAACTACTGATATCTTAAACATGACACACATCATG

AGCCTGAATTCCAATGAAAAGTCATTAAAATTATCACCAGTTCAGAAACAAAAGAAACAACAAACAATT

GGGGAACTGACGCAGGATACAGCTCTTACTGAAAACGATGATAGTGATGAATATGAAGAAATGTCAGAA

ATGAAAGAAGGGAAAGCATGTAAACAACATGTGTCACAAGGGATTTTCATGACGCAGCCAGCTACGACT

ATCGAAGCATTTTCAGATGAGGAAGTAGAGATCCCAGAGGAGAAGGAAGGAGCAGAGGATTCAAAGGA

AATGGAATAGAGGAGCAAGAGGTAGAAGCAAATGAGGAAAATGTGAAGGTGCATGGAGGAAGAAAGGAG

AAAACAGAGATCCTATCAGATGACCTTACAGACAAAGCAGAGGTGAGTGAAGGCAAGGCAAAATCAGTG

GGAGAAGCAGAGGATGGGCCTGAAGGTAGAGGGGATGGAACCTGTGAGGAAGGTAGTTCAGGAGCAGAA

CACTGGCAAGATGAGGAGAGGGAGAAGGGGGAGAAAGACAAGGGTAGAGGAGAAATGGAGAGGCCAGGA

GAGGGAGAGAAGGAACTAGCAGAGAAGGAAGAATGGAAGAAGAGGGATGGGGAAGAGCAGGAGCAAAAG

GAGAGGGAGCAGGGCCATCAGAAGGAAAGAAACCAAGAGATGGAGGAGGGAGGGAGGAGGAGCATGGA

GAAGGAGAAGAAGAGGAGGGAGACAGAGAAGAGGAAGAAGAGAAGGAGGGAGAAGGGAAGAGGAAGGA

GAAGGGGAAGAAGTGGAGGGAGAACGTGAAAAGGAGGAAGGAGAGAGGAAAAAGGAGGAAAGAGCGGGG

AAGGAGGAGAAAGGAGAGGAAGAAGGAGAGACCAAGGAGAGGGGGAAGAGGAGGAAACAGAGGGGAGAGGG

GAGGAAAAAGAGGAGGGAGGGGAAGTAGGGGAGGGGAAGTAGAGGAGGGGAAAGGAGAGAGGGAAGAG

GAAGAGGAGGAGGGTGAGGGGGAAGAGGAGGAAGGGGAGGGGGAAGAGGAGGAAGGGGAGGGGGAAGAG

-continued

```
GAGGAAGGAGAAGGGAAAGGGGAGGAAGAAGGGGAAGAAGGAGAAGGGGAGGAAGAAGGGGAGGAAGGA

GAAGGGGAGGGGGAAGAGGAGGAAGGAGAAGGGGAGGGAGAAGAGGAAGGAGAAGGGGAGGGAGAAGAG

GAGGAAGGAGAAGGGGAGGGAGAAGAGGAAGGAGAAGGGGAGGGAGAAGAGGAGGAAGGAGAAGGGAAA

GGGGAGGAGGAAGGAGAGGAAGGAGAAGGGGAGGGGGAAGAGGAGGAAGGAGAAGGGGAAGGGGAGGAT

GGAGAAGGGGAGGGGGAAGAGGAGGAAGGAGAATGGGAGGGGGAAGAGGAGGAAGGAGAAGGGGAGGGG

GAAGAGGAAGGAGAAGGGGAAGGGGAGGAAGGAGAAGGGGAGGGGGAAGAGGAGGAAGGAGAAGGGGAG

GGGGAAGAGGAGGAAGGGGAAGAAGAAGGGGAGGAAGAAGGAGAGGGAGAGGAAGAAGGGGAGGGAGAA

GGGGAGGAAGAAGAGGAAGGGGAAGTGGAAGGGGAGGTGGAAGGGGAGGAAGGAGAGGGGAAGGAGAG

GAAGAGGAAGGAGAGGAGGAAGGAGAAGAAAGGGAAAAGGAGGGGAAGGAGAAGAAACAGGAGGAAC

AGAGAAGAGGAGGAGGAAGAAGAGGGGAAGTATCAGGAGACAGGCGAAGAAGAGAATGAAAGGCAGGAT

GGAGAGGAGTACAAAAAAGTGAGCAAAATAAAAGGATCTGTGAAATATGGCAAACATAAAACATATCAA

AAAAAGTCAGTTACTAACACACAGGGAAATGGGAAAGAGCAGAGGTCCAAAATGCCAGTCCAGTCAAAA

CGACTTTTAAAAAATGGGCCATCAGGTTCCAAAAAGTTCTGGAATAATATATTACCACATTACTTGGAA

TTGAAGTAA
```

Full-Length Human RPGRORF15 amino acid sequence; amino acids deleted
in Abbreviated form are bolded and underlined in sequence below

```
atgagggagccggaagagctgatgcccgattcgggtgctgtgtttacatttgggaaaagt
 M  R  E  P  E  E  L  M  P  D  S  G  A  V  F  T  F  G  K  S aaatttgctgaaaataatcccggtaaattctggtttaaaaatgatgtccctgtacatctt
 K  F  A  E  N  N  P  G  K  F  W  F  K  N  D  V  P  V  H  L tcatgtggagatgaacattctgctgttgttaccggaaataataaactttacatgtttggc
 S  C  G  D  E  H  S  A  V  V  T  G  N  N  K  L  Y  M  F  G agtaacaactggggtcagttaggattaggatcaaagtcagccatcagcaagccaacatgt
 S  N  N  W  G  Q  L  G  L  G  S  K  S  A  T  S  K  P  T  C gtcaaagctctaaaacctgaaaaagtgaaattagctgcctgtggaaggaaccacaccctg
 V  K  A  L  K  P  E  K  V  K  L  A  A  C  G  R  N  H  T  L gtgtcaacagaaggaggcaatgtatatgcaactggtggaaataatgaaggacagttgggg
 V  S  T  E  G  G  N  V  Y  A  T  G  G  N  N  E  G  Q  L  G cttggtgacaccgaagaaagaaacacttttcatgtaattagcttttttacatccgagcat
 L  G  D  T  E  E  R  N  T  F  H  V  I  S  F  F  T  S  E  H aagattaagcagctgtctgctggatctaatacttcagctgccctaactgaggatggaaga
 K  I  K  Q  L  S  A  G  S  N  T  S  A  A  L  T  E  D  G  R ctttttatgtggggtgacaattccgaagggcaaattggtttaaaaaatgtaagtaatgtc
 L  F  M  W  G  D  N  S  E  G  Q  I  G  L  K  N  V  S  N  V tgtgtccctcagcaagtgaccattgggaaacctgtctcctggatctcttgtggatattac
 C  V  P  Q  Q  V  T  I  G  K  P  V  S  W  I  S  C  G  Y  Y cattcagcttttgtaacaacagatggtgagctatatgtgtttggagaacctgagaatggg
 H  S  A  F  V  T  T  D  G  E  L  Y  V  F  P  E  N  E  N  G aagttaggtcttcccaatcagctcctgggcaatcacagaacaccccagctggtgtctgaa
 K  L  G  L  P  N  Q  L  L  G  N  H  R  T  P  Q  L  V  S  E attccggagaaggtgatccaagtagcctgtggtggagagcatactgtggttctcacggag
 I  P  E  K  V  I  Q  V  A  C  G  G  E  H  T  V  V  L  T  E aatgctgtgtataccttttgggctgggacaatttggtcagctgggtcttggcacttttctt
 N  A  V  Y  T  F  G  L  G  Q  F  G  Q  L  G  L  G  T  F  L tttgaaacttcagaacccaaagtcattgagaatattagggatcaaacaataagttatatt
 F  E  T  S  E  P  K  V  I  E  N  I  R  D  Q  T  I  S  Y  I tcttgtggagaaaatcacacagctttgataacagatatcggccttatgtatacttttgga
 S  C  G  E  N  H  T  L  I  T  T  D  I  G  L  M  Y  T  F  G gatggtcgccacggaaaattaggacttggactggagaattttaccaatcacttcattcct
 D  G  R  H  G  K  L  G  L  G  L  E  N  F  T  N  H  F  I  P
```

```
actttgtgctctaattttttgaggtttatagttaaattggttgcttgtggtggatgtcac
 T  L  C  S  N  F  L  R  F  I  V  K  L  V  A  C  G  G  C  H atggtagttttgctgctcctcatcgtggtgtggcaaaagaaattgaattcgatgaaata
 M  V  V  F  A  A  P  H  R  G  V  A  K  E  I  E  F  D  E  I aatgatacttgcttatctgtggcgacttttctgccgtatagcagtttaacctcaggaaat
 N  D  T  C  L  S  V  A  T  F  L  P  Y  S  S  L  T  S  G  N gtactgcagaggactctatcagcacgtatgcggcgaagagagagggagaggtctccagat
 V  L  Q  R  T  L  S  A  R  M  R  R  R  E  R  E  R  S  P  D tcttttcaatgaggagaacactacctccaatagaagggactcttggcctttctgcttgt
 S  F  S  M  R  R  T  L  P  P  I  E  G  T  L  G  L  S  A  C tttctccccaattcagtctttccacgatgttctgagagaaacctccaagagagtgtctta
 F  L  P  N  S  V  F  P  R  C  S  E  R  N  L  Q  E  S  V  L tctgaacaggacctcatgcagccagaggaaccagattatttgctagatgaaatgaccaaa
 S  E  Q  D  L  M  Q  P  E  E  P  D  Y  L  L  D  E  M  T  K gaagcagagatagataattcttcaactgtagaaagccttggagaaactactgatatctta
 E  A  E  I  D  N  S  S  T  V  E  S  L  G  E  T  T  D  I  L aacatgacacacatcatgagcctgaattccaatgaaaagtcattaaaattatcaccagtt
 N  M  T  H  I  M  S  L  N  S  N  E  K  S  L  K  L  S  P  V cagaaacaaaagaaacaacaaacaattggggaactgacgcaggatacagctcttactgaa
 Q  K  Q  K  K  Q  Q  T  I  G  E  L  T  Q  D  T  A  L  T  E aacgatgatagtgatgaatatgaagaaatgtcagaaatgaaagaagggaaagcatgtaaa
 N  D  D  S  D  E  Y  E  E  M  S  K  E  G  E  G  K  A  C  K caacatgtgtcacaagggatttttcatgacgcagccagctacgactatcgaagcattttca
 Q  H  V  S  Q  G  I  F  M  T  P  A  T  T  I  I  E  A  F  S gatgaggaagtagagatcccagaggagaaggaaggagcagaggattcaaaaggaaatgga
 D  E  E  V  E  I  P  E  E  K  E  G  A  E  D  S  K  G  N  G atagaggagcaagaggtagaagcaaatgaggaaaatgtgaaggtgcatggaggaagaaag
 I  E  E  Q  E  V  E  A  N  E  E  N  V  K  V  H  G  G  R  K gagaaaacagagatcctatcagatgaccttacagacaaagcagaggtgagtgaaggcaag
 E  K  T  E  I  L  S  D  D  L  T  D  K  A  E  V  S  E  G  K gcaaaatcagtgggagaagcagaggatgggcctgaaggtagaggggatggaacctgtgag
 A  K  S  V  G  E  A  E  D  G  P  E  G  R  G  D  G  T  C  E gaaggtagttcaggagcagaacactggcaagatgaggagagggagaaggggagaaagac
 E  G  S  S  G  A  E  H  W  Q  D  E  E  R  E  K  G  E  K  D aagggtagaggagaaatggagaggccaggagagggagagaaggaactagcagagaaggaa
 K  G  R  G  E  M  E  R  P  G  E  G  E  K  E  L  A  E  K  E gaatggaagaagagggatggggaagagcaggagcaaaaggagagggagcagggccatcag
 E  W  K  K  R  D  G  E  E  Q  E  Q  K  E  R  E  Q  G  H  Q aaggaaagaaaccaagagatggaggagggaggggaggaggagcatggagaaggagaagaa
 K  E  R  N  Q  E  M  E  E  G  G  E  E  E  H  G  E  G  E  E gaggagggagacagagaagaggaagaagaagaaggagggagaagggaaagaggaaggagaa
 E  E  G  D  R  E  E  E  E  K  E  G  E  G  K  E  E  G  E ggggaagaagtggagggagaacgtgaaaaggaggaaggagagaggaaaaaggaggaaaga
 G  E  E  V  E  G  E  R  E  K  E  E  G  E  R  K  K  E  E  R gcggggaaggaggagaaaggagaggaagaaggagaccaaggagaggggaagaggaggaa
 A  G  K  E  E  K  G  E  E  E  G  D  Q  G  E  G  E  E  E  E acagaggggagaggggaggaaaaagaggagggaggggaagtagagggaggggaagtagag
 T  E  G  R  G  E  E  K  E  E  G  G  E  V  E  G  G  E  V  E gaggggaaggagagagggaagaggaagaggaggagggtgaggggaagaggaggaaggg
 E  G  K  G  E  R  E  E  E  E  E  G  E  G  E  E  E  E  G gaggggaagaggaggaagggagggggaagaggaggaaggagaagggaaaggggaggaa
 E  G  E  E  E  E  G  E  G  E  E  E  E  G  E  G  K  G  E  E gaagggaagaaggagaagggaggaagaaggggaggaaggagaaggggaggggaagag
 E  G  E  E  G  E  G  E  E  E  G  E  E  G  E  G  E  G  E  E
```

-continued

```
gaggaaggagaaggggaggggagaagaggaaggagaaggggagggagaagaggaggaagga
 E   E   G   E   G   E   E   E   G   E   G   E   G   E   E   E   G gaagggagggagaagaggaaggagaaggggagggagaagaggaggaaggagaagggaaa
 E   G   E   G   E   E   E   G   E   G   E   G   E   E   E   G   E   G   K ggggaggaggaaggagaggaaggagaaggggagggggaagaggaggaaggagaaggggaa
 G   E   E   E   G   E   E   G   E   G   E   G   E   E   E   E   G   E   G   E ggggaggatggagaaggggaggggaagaggaggaaggagaatggagggggaagaggag
 G   E   D   G   E   G   E   G   E   E   E   E   G   E   W   E   G   E   E   E gaaggagaaggggaggggaagaggaaggagaaggggaagggggaggaaggagaaggggag
 E   G   E   G   E   E   E   G   E   G   E   G   E   E   G   E   G   E ggggaagaggaggaaggagaagggagggggaagaggaggaaggggaagaagaagggag
 G   E   E   E   G   E   G   E   G   E   E   E   E   G   E   E   E   G   E gaagaaggagagggagaggaagaagggggagggagaagggggaggaagaagaggaagggggaa
 E   E   G   E   G   E   E   E   G   E   G   E   G   E   E   E   E   G   E gtggaagggggaggtggaaggggaggaaggagagggggaaggagaggaagaggaaggagag
 V   E   G   E   V   E   G   E   E   G   E   G   E   G   E   E   E   E   G   E gaggaaggagaagaaagggaaaaggaggggggaaggagaagaaaacaggaggaacagagaa
 E   E   G   E   E   R   E   K   E   G   E   G   E   E   N   R   R   N   R   E gaggaggaggaagaaggggggaagtatcaggagacaggcgaagaagagaatgaaaggcag
 E   E   E   E   E   G   K   Y   Q   E   T   G   E   E   E   N   E   R   Q gatggagaggagtacaaaaaagtgagcaaaataaaaggatctgtgaaatatggcaaacat
 D   G   E   E   Y   K   K   V   S   K   I   K   G   S   V   K   Y   G   K   H aaaacatatcaaaaaaagtcagttactaacacacagggaaatgggaaagagcagaggtcc
 K   T   Y   Q   K   K   S   V   T   N   T   Q   G   N   G   K   E   Q   R   S aaaatgccagtccagtcaaaacgacttttaaaaaatgggccatcaggttccaaaaagttc
 K   M   P   V   Q   S   K   R   L   L   K   N   G   P   S   G   S   K   K   F tggaataatatattaccacattacttggaattgaagtaa (SEQ ID NO: 3)
 W   N   N   I   L   P   H   Y   L   E   L   K   -  (SEQ ID NO:4)
```

The comparison of sequences and determination of percent identity between two sequences can be accomplished using a mathematical algorithm. For example, the percent identity between two amino acid sequences can determined using the Needleman and Wunsch ((1970) J. Mol. Biol. 48:444-453) algorithm which has been incorporated into the GAP program in the GCG software package (available on the world wide web at gcg.com), using the default parameters, e.g., a Blossum 62 scoring matrix with a gap penalty of 12, a gap extend penalty of 4, and a frameshift gap penalty of 5.

RK Promoter

In some embodiments of the methods described herein, a replacement gene construct is used in which an abbreviated human RPGR cDNA as described herein is placed under the control of a human rhodopsin kinase (hRK) promoter. In some embodiments, the RK promoter is approx. 200 bp in length (a short promoter derived from the rhodopsin kinase (RK) gene, which has been shown to drive cell-specific expression in rods and cones (Khani et al., 2007; Sun et al., 2010; Young et al., 2003)). An exemplary hRK promoter sequence is -112/+87 (Khani et al., 2007):

```
                                              (SEQ ID NO: 5)
GGGCCCAGAAGCCTGGTGGTTGTTTGTCCTTCTCAGGGGAAAAGTGAG

GCGGCCCCTTGGAGGAAGGGGCCGGGCAGAATGATCTAATCGGATTCCA

AGCAGCTCAGGGGATTGTCTTTTTCTAGCACCTTCTTGCCACTCCTAAG

CGTCCTCCGTGACCCCGGCTGGGATTTAGCCTGGTGCTGTGTCAGCCCC

GGT
```

Viral Delivery Vector

The abbreviated human RPGR cDNA, as described above, is packaged into a delivery vector, e.g., an AAV8 or AAV2/8 vector.

Replacement genes (cDNA) can be administered in any effective carrier, e.g., any formulation or composition capable of effectively delivering the component gene to cells in vivo. Approaches include insertion of the gene into non-pathogenic, non-replicating viral vectors, including recombinant retroviruses, adenovirus, adeno-associated virus, lentivirus, and herpes simplex virus-1, or recombinant bacterial or eukaryotic plasmids. Viral vectors transfect cells directly; plasmid DNA can be delivered naked or with the help of, for example, cationic liposomes (lipofectamine) or derivatized (e.g., antibody conjugated), polylysine conjugates, gramacidin S, artificial viral envelopes or other such intracellular carriers, as well as direct injection of the gene construct or $CaPO_4$ precipitation carried out in vivo.

A preferred approach for in vivo introduction of nucleic acid into a cell is by use of a viral vector containing nucleic acid, e.g., a cDNA. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells that have taken up viral vector nucleic acid.

Retrovirus vectors and adeno-associated virus vectors can be used as a recombinant gene delivery system for the transfer of exogenous genes in vivo, particularly into humans. These vectors provide efficient delivery of genes into cells, and the transferred nucleic acids are stably integrated into the chromosomal DNA of the host. The development of specialized cell lines (termed "packaging cells") which produce only replication-defective retroviruses has increased the utility of retroviruses for gene therapy, and defective retroviruses are characterized for use in gene transfer for gene therapy purposes (for a review see Miller, *Blood* 76:271 (1990)). A replication defective retrovirus can be packaged into virions, which can be used to infect a target cell through the use of a helper virus by standard techniques. Protocols for producing recombinant retroviruses and for infecting cells in vitro or in vivo with such viruses can be found in Ausubel, et al., eds., *Current Protocols in Molecular Biology*, Greene Publishing Associates, (1989), Sections 9.10-9.14, and other standard laboratory manuals. Examples of suitable retroviruses include pLJ, pZIP, pWE and pEM which are known to those skilled in the art. Examples of suitable packaging virus lines for preparing both ecotropic and amphotropic retroviral systems include ΨCrip, ΨCre, Ψ2 and ΨAm. Retroviruses have been used to introduce a variety of genes into many different cell types, including epithelial cells, in vitro and/or in vivo (see for example Eglitis, et al. (1985) Science 230:1395-1398; Danos and Mulligan (1988) Proc. Natl. Acad. Sci. USA 85:6460-6464; Wilson et al. (1988) Proc. Natl. Acad. Sci. USA 85:3014-3018; Armentano et al. (1990) Proc. Natl. Acad.

Sci. USA 87:6141-6145; Huber et al. (1991) Proc. Natl. Acad. Sci. USA 88:8039-8043; Ferry et al. (1991) Proc. Natl. Acad. Sci. USA 88:8377-8381; Chowdhury et al. (1991) Science 254:1802-1805; van Beusechem et al. (1992) Proc. Natl. Acad. Sci. USA 89:7640-7644; Kay et al. (1992) Human Gene Therapy 3:641-647; Dai et al. (1992) Proc. Natl. Acad. Sci. USA 89:10892-10895; Hwu et al. (1993) J. Immunol. 150:4104-4115; U.S. Pat. No. 4,868,116; U.S. Pat. No. 4,980,286; PCT Application WO 89/07136; PCT Application WO 89/02468; PCT Application WO 89/05345; and PCT Application WO 92/07573).

Another viral gene delivery system useful in the present methods utilizes adenovirus-derived vectors. The genome of an adenovirus can be manipulated, such that it encodes and expresses a gene product of interest but is inactivated in terms of its ability to replicate in a normal lytic viral life cycle. See, for example, Berkner et al., BioTechniques 6:616 (1988); Rosenfeld et al., Science 252:431-434 (1991); and Rosenfeld et al., Cell 68:143-155 (1992). Suitable adenoviral vectors derived from the adenovirus strain Ad type 5 d1324 or other strains of adenovirus (e.g., Ad2, Ad3, or Ad7 etc.) are known to those skilled in the art. Recombinant adenoviruses can be advantageous in certain circumstances, in that they are not capable of infecting non-dividing cells and can be used to infect a wide variety of cell types, including epithelial cells (Rosenfeld et al., (1992) supra). Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situ, where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al., supra; Haj-Ahmand and Graham, J. Virol. 57:267 (1986).

Yet another viral vector system useful for delivery of nucleic acids is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al., Curr. Topics in Micro. and Immunol.158:97-129 (1992). It is also one of the few viruses that may integrate its DNA into non-dividing cells, and exhibits a high frequency of stable integration (see for example Flotte et al., Am. J. Respir. Cell. Mol. Biol. 7:349-356 (1992); Samulski et al., J. Virol. 63:3822-3828 (1989); and McLaughlin et al., J. Virol. 62:1963-1973 (1989). Vectors containing as little as 300 base pairs of AAV can be packaged and can integrate. Space for exogenous DNA is limited to about 4.5 kb. An AAV vector such as that described in Tratschin et al., Mol. Cell. Biol. 5:3251-3260 (1985) can be used to introduce DNA into cells. A variety of nucleic acids have been introduced into different cell types using AAV vectors (see for example Hermonat et al., Proc. Natl. Acad. Sci. USA 81:6466-6470 (1984); Tratschin et al., Mol. Cell. Biol. 4:2072-2081 (1985); Wondisford et al., Mol. Endocrinol. 2:32-39 (1988); Tratschin et al., J. Virol. 51:611-619 (1984); and Flotte et al., J. Biol. Chem. 268:3781-3790 (1993).

In preferred embodiments, the viral delivery vector is a recombinant AAV2/8 virus.

Prior to administration, the final product will undergo a series of ultrapurification steps to meet clinical grade criteria.

Subject Selection

Subjects who are candidates for the present methods of treatment include those who have a diagnosis of RP caused by mutations in the gene encoding RPGR. Subjects suffering from other ophthalmological clinically-defined conditions caused by mutations in the gene encoding RPGR, e.g., X-linked cone-rod dystrophy, can also be treated using the methods described herein. A diagnosis of XLRP or another ophthalmological condition caused by mutations in the gene encoding RPGR can be made using methods known in the art.

The methods described herein can include identifying a subject, e.g., a child, adolescent, or young adult subject, who has XLRP or another ophthalmological condition caused by mutations in the gene encoding RPGR, or who is suspected of having XLRP or another ophthalmological condition caused by mutations in the gene encoding RPGR (e.g., based on the presence of symptoms of the condition and no other obvious cause), and obtaining a sample comprising genomic DNA from the subject, detecting the presence of a mutation in RPGR using known molecular biological methods, and selecting a patient who has a mutation in RPGR that causes XLRP or another condition. Detecting a mutation in RPGR can include detecting a mutation in ORF15, e.g., as described in Sandberg et al., (2007). Invest Ophthalmol Vis Sci 48, 1298-304; Dror et al., Am J Hum Genet. November 2003; 73(5): 1131-1146.

Mutations in RPGR ORF15 include frameshift mutations, nonsense mutations, splice-site mutations, and missesnse mutations. Exemplary mutations include ORF15Glu446 (1-bp-del), ORF15Glu447 (2-bp-del), and ORF15GLys521 (1-bp-ins).

Detecting a mutation in RPGR can also include sequencing all or part of (e.g., the ORF15 region) the RPGR gene in a subject, and comparing the sequence to a reference sequence (e.g., GenBank Accession No. NG_009553.1), to detect a mutation. Frameshift mutations, truncation mutations, mutations that alter a conserved amino acid, or mutations that affect a regulatory (e.g., promoter) region can be considered to be mutations that can cause XLRP or another ophthalmological condition as described herein; an alteration in function can be confirmed by expressing the mutant in vitro (e.g., in cultured cells) or in vivo (e.g., in a transgenic animal), and assaying, e.g., function or subcellular localization.

Patients with XLRP or another ophthalmological condition due to RPGR mutations that can be treated using a method described herein preferably retain some photoreceptors and visual function, e.g., as measured by standard visual function or field tests and/or Optical Coherence Tomography (OCT, e.g., Spectral Domain-OCT (SD-OCT)); see, e.g., Sandberg et al., Invest Ophthalmol Vis Sci. 2007;48:1298-1304. The methods described herein can include identifying subjects who have been diagnosed with XLRP or another ophthalmological condition due to RPGR mutations, who have a confirmed mutation in RPGR that causes their condition, and testing their visual ability and detecting the presence of residual central photoreceptors. Subjects, e.g., child, adolescent, young adult, or adult subjects, who can be treated using the present methods will preferably have visual acuity of at least 20/200 (methods for determining visual acuity are well known in the art; see, e.g., Johnson, *Deafness and Vision Disorders: Anatomy and Physiology, Assessment Procedures, Ocular Anomalies, and Educational Implications,* Charles C. Thomas Publisher; 1999) Carlson, N; Kurtz, D.; Heath, D.; Hines, C. *Clinical Procedures for Ocular Examination.* Appleton & Lange; Norwalk, Conn. 1990) and a detectable outer nuclear layer in the central fovea (e.g., at least 75%, 80%, 90%, 95%, or 99% of normal thickness).

EXAMPLES

The invention is further described in the following examples, which do not limit the scope of the invention described in the claims.

Materials and Methods

The following materials and methods were used in the Examples set forth below.

Animals

The generation and analysis of RPGR$^{-/-}$ mice have been described previously (Hong and others 2000). The RPGR$^{-/-}$ mice used in this study were bred from sibling mating among nullizygous RPGR males and homozygous (RPGR$^{-/-}$) females maintained in our institutional animal facility. WT mice used in the study were C57BL from Charles River Laboratory (Wilmington, Mass.). Mice were maintained under 12 hr light/12 hr dark lighting cycle. The studies were done in accordance with the ARVO Statement for the Use of Animals in Ophthalmic and Vision Research, and approved by the IACUC of the Massachusetts Eye and Ear Infirmary.

Plasmid Construction and Production of Recombinant AAV8

Human RPGR ORF15 cDNA were amplified from human retinal cDNA by PCR using primers designed to encompass the entire RPGR ORF15 isoform coding region. No full-length ORF15 cDNAs were obtained despite repeated attempts using a variety of methods, consistent with the experience of other investigators and that of our own (Hong and others 2005). Instead, we obtained an abbreviated ORF15 cDNA containing a large 314 codon (942 bp) in-frame deletion in the ORF15 exon (2,517-bp remaining) with the bulk of the purine rich repetitive region removed (codons 696-1010del, "short form") (FIG. 1A). A second ORF15 cDNA was constructed through recombinant DNA manipulation which contained a 126-codon (378 bp) in-frame deletion within the highly repetitive region of exon 15 (with 3,081-bp remaining in the ORF15 exon) (codons 862-988del,"long form"). These ORF15 cDNAs were sequenced to verify fidelity. To construct the AAV vectors, RPGR cDNAs were inserted into the multiple cloning site of the parental pAAV-RK-zsGreen vector. The resulting pAAV-RK-mRPGR and pAAV-RK-hRPGR vectors were packaged into AAV. AAV2/8 pseudotyped vector was generated by tripartite transfection: (1) AAV vector plasmid encoding the gene of interest, (2) AAV helper plasmid pLT-RCO3 encoding AAV Rep proteins from serotype 2 and Cap proteins from serotype 8, and (3) adenovirus helper miniplasmid pHGTI-Adeno1) into 293A cells. The transfection was performed using a protocol developed by Xiao and co-workers (Xiao, et al., 1998). Two days after transfection, cells were lysed by repeated freeze and thaw cycles. After initial clearing of cell debris, the nucleic acid component of the virus producer cells was removed by Benzonase treatment. The recombinant AAV vector particles were purified by iodixanol density gradient. The purified vector particles were dialyzed extensively against PBS and tittered by dot blot hybridization.

Subretinal Injections

Mice were placed under general anaesthesia with an intraperitoneal injection of ketamine (90 mg/kg)/xylazine (9 mg/kg). A 0.5% proparacaine solution was applied to the cornea as a topical anesthetic. Pupils were dilated with topical application of cyclopentolate and phenylephrine hydrochloride. Under an ophthalmic surgical microscope, a small incision was made through the cornea adjacent to the limbus using an 18-gauge needle. A 33-gauge blunt needle fitted to a Hamilton syringe was inserted through the incision behind the lens and pushed through the retina. All injections were made subretinally in a location within the nasal quadrant of the retina. Injections were made subretinally within the nasal quadrant of the retina. Each eye received either 2×10$^9$ vector genome (AAV-ORF15-L) or 5×10$^9$ vector genome (AAV-ORF15-S) in a 1 μl volume. RPGR-ORF15 vectors were administered to the left eye (OS, oculus sinister) and control vector (AAV8-RK-EGFP) were administered to the right eye (OD, oculus dexter). These are referred throughout this text as "treated" or "control", respectively. Visualization during injection was aided by the addition of fluorescein (100 mg/ml AK-FLUOR, Alcon, Inc.) to the vector suspensions at 0.1% by volume. Fundus examination following the injection found >30% of the retina detached in most cases, confirming successful subretinal delivery. Cohorts of mice (n=50 total) were injected at 1 month of age for protein expression studies and at 3 to 7 months of age (since ERGs remained normal during this age period) for functional (ERG) and histological studies, prior to major photoreceptor loss.

Histology and Immunofluorescence

For both light microscopy and transmission electron microscopy, enucleated eyes were fixed for 10 minutes in 1% formaldehyde, 2.5% glutaraldehyde in 0.1 M cacodylate buffer (pH7.5). Following removal of the anterior segments and lens, the eyecups were left in the same fixative at 4° C. overnight. Eye cups were washed with buffer, post-fixed in osmium tetroxide, dehydrated through a graded alcohol series and embedded in Epon. Semi-thin sections (1 μm) were cut for light microscopy observations. For EM, ultra-thin sections were stained in uranyl acetate and lead citrate before viewing on a JEOL 100CX electron microscope.

For immunofluorescence staining of ciliary proteins, eyes were enucleated, shock frozen, and sectioned at 10-μm thick in a cryostat. Unfixed frozen sections were then collected on glass and stained. For immunostaining of all other proteins, floating retinal sections were collected and stained. For this process eyes were placed in fixative (2% formaldehyde, 0.25% glutaraldehyde/PBS) and their anterior segments and lens were removed. Duration of fixation was typically 20 minutes. The fixed tissues were soaked in 30% sucrose/PBS for at least 2 hours, shock frozen and sectioned similar to unfixed tissues. Sections were then collected into PBS buffer and remained free floating for the duration of the immunostaining process. Stained sections were viewed and photographed on a laser scanning confocal microscope (model TCS SP2; Leica). Antibodies used were mouse RPGR (S1), human RPGR C100, anti-rootletin, 1D4 (anti-rhodopsin), mixed blue/green cone anti-opsin, and Hoechst 33342, nuclear dye stain.

Immunoblotting Analysis

Retinal tissues were homogenized in RIPA buffer, boiled in Laemmli buffer and loaded at 15 µg/lane on 5% SDS-PAGE gels. After gel separation, proteins were blotted to PVDF membrane by electrotransfer. The membranes were blocked with 5% non-fat milk and incubated with primary antibodies overnight at room temperature. After washing, membranes were incubated with peroxidase-conjugated secondary antibodies. SuperSignal® West Pico Chemiluminescent Substrate (Pierce) was used for detection. For normalization, protein samples were separated on standard SDS-PAGE and probed with a transducin α antibody (gift of Dr. Heidi Hamm, Vanderbilt University).

ERG Recording

Mice were dark-adapted overnight and anesthetized with sodium pentobarbital injected intraperitoneally prior to testing. Both pupils of each animal were topically dilated with phenylephrine hydrochloride and cyclopentolate hydrochloride, and mice were then placed on a heated platform. Rod dominated responses were elicited in the dark with 10-µs flashes of white light ($1.37 \times 10^5$ cd/m$^2$) presented at intervals of 1 minute in a Ganzfeld dome. Light-adapted, cone responses were elicited in the presence of a 41 cd/m$^2$ rod-desensitizing white background with the same flashes ($1.37 \times 10^5$ cd/m$^2$) presented at intervals of 1 Hz. ERGs were monitored simultaneously from both eyes with a silver wire loop electrode in contact with each cornea topically anesthetized with proparacaine hydrochloride and wetted with Goniosol, with a subdermal electrode in the neck as the reference; an electrically-shielded chamber served as ground.

All responses were differentially amplified at a gain of 1,000 (−3 db at 2 Hz and 300 Hz; AM502, Tektronix Instruments, Beaverton, Oreg.), digitized at 16-bit resolution with an adjustable peak-to-peak input amplitude (PCI-6251, National Instruments, Austin, Tex.), and displayed on a personal computer using custom software (Labview, version 8.2, National Instruments). Independently for each eye, cone responses were conditioned by a 60 Hz notch filter and an adjustable artifact-reject window, summed (n=4-20), and then fitted to a cubic spline function with variable stiffness to improve signal:noise without affecting their temporal characteristics; in this way we could resolve cone b-wave responses as small as 2 µV.

Statistical Analysis

JMP, version 6 (SAS Institute, Cary, N.C.) was used to compare cross-sectional ERG amplitudes and implicit times. Repeated—measures analyses with PROC MIXED OF SAS, version 9.3 (SAS Institute) were used for histologic comparisons and for comparing longitudinal ERG data of treated versus untreated eyes.

Patients

Full-field electroretinographic (ERG) data, obtained from the dataset described by Sharon, et al (2003), for 111 patients with XLRP due to ORF15 RPGR mutations were reviewed to compare b-wave amplitudes to 0.5 Hz white light, which reflect remaining rod+cone function, and to 30 Hz flashes of the same white light, which reflect remaining cone function alone. To determine whether they had rod-cone or cone-rod disease, we calculated the ratio of their amplitude to 0.5 Hz flashes divided by their amplitude to 30 Hz flashes for OD and for OS; the same ratio for the lower limit of normal in our system is 350 µV/50 µV=7. For more precise quantification of response amplitudes to 0.5 Hz flashes and to minimize possible effects secondary to the primary photoreceptor degeneration, we focused on those patients (n=14) with amplitudes to 0.5 Hz flashes>50 µV that reflected earlier or milder disease.

ERGs of Patients with ORF15 Mutations

Figure 6:
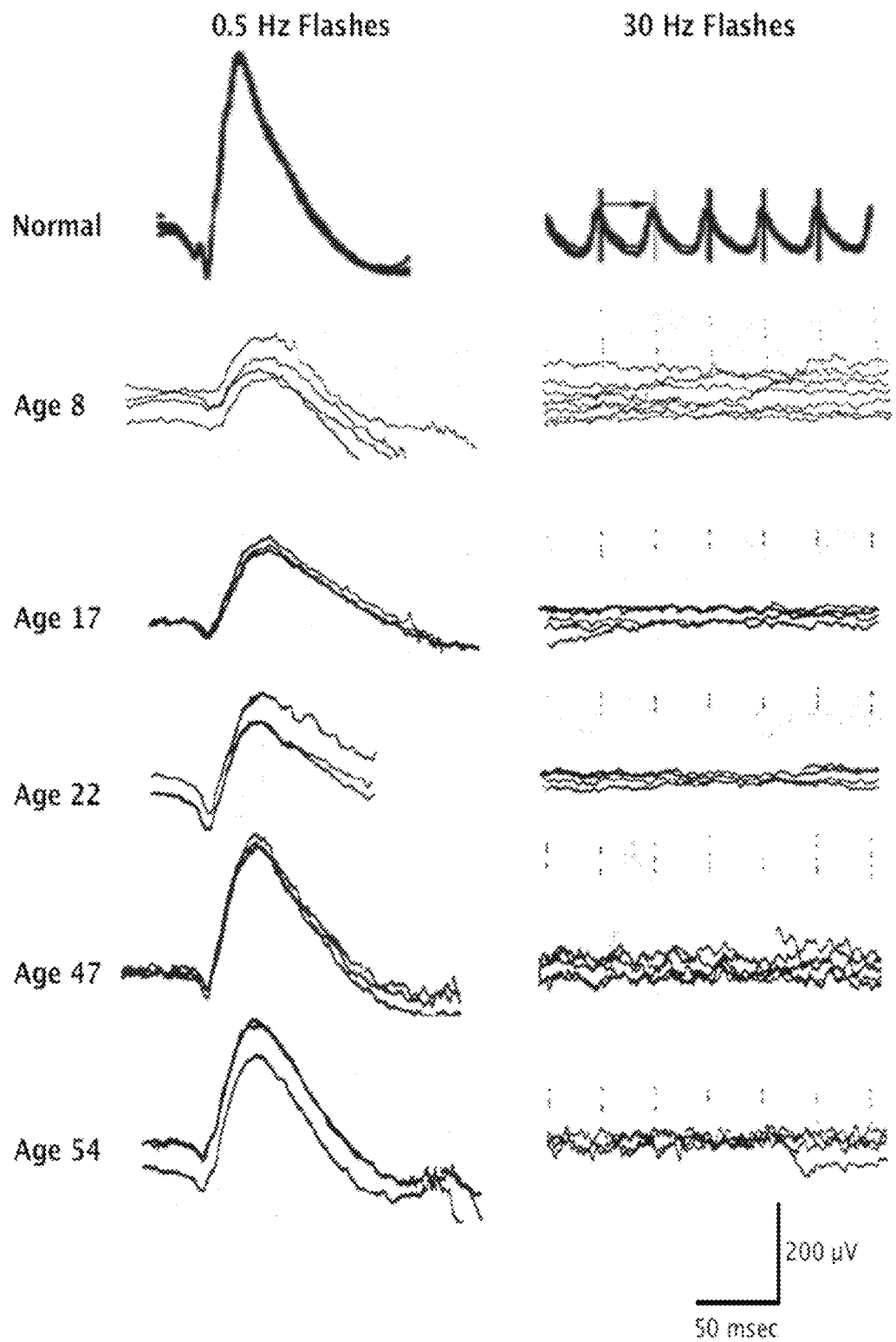
FIG. 6. Full-field ERGs to 0.5 Hz flashes of white light and to 30 Hz flashes of the same white light from 5 patients with XLRP due to RPGR ORF15 mutations. Three or more traces are superimposed to illustrate reproducibility. Dots above traces designate flash onset. While the responses to 0.5 Hz responses were reduced by only 6% to 65% below the lower limit of normal (350 µV), the responses to 30 Hz flashes were nondetectable as illustrated (i.e., without bandpass filtering and signal averaging).

For the 14 patients with the most robust responses to 0.5 Hz white flashes, reflecting remaining rod+cone function, amplitudes to that condition ranged from 53 µV to 329 µV OD and from 59 µV to 282 µV OS. Their amplitudes to 30 Hz flashes of the same white light, reflecting cone function alone and monitored with bandpass filtering and signal averaging for amplitudes<10 µV, ranged from 0.98 µV to 23.5 µV OD and from 0.95 µV to 20 µV OS. The ratio of response amplitude to 0.5 Hz flashes divided by response amplitude to 30 Hz flashes had a mean±standard error of 47.0±12.7 OD and 48.7±13.0 OS. These mean values were significantly different from 7.0, the value for the ratio based on the lower limits of normal (nonparametric signed-rank test, p=0.0004 OD and p=0.001 OS). In other words, these patients with ORF15 mutations had markedly disproportionate loss of cone function. Examples of these ERGs are shown in FIG. 6.

Example 1

AAV-Mediated Expression of Human RPGR ORF15

Figure 1B:
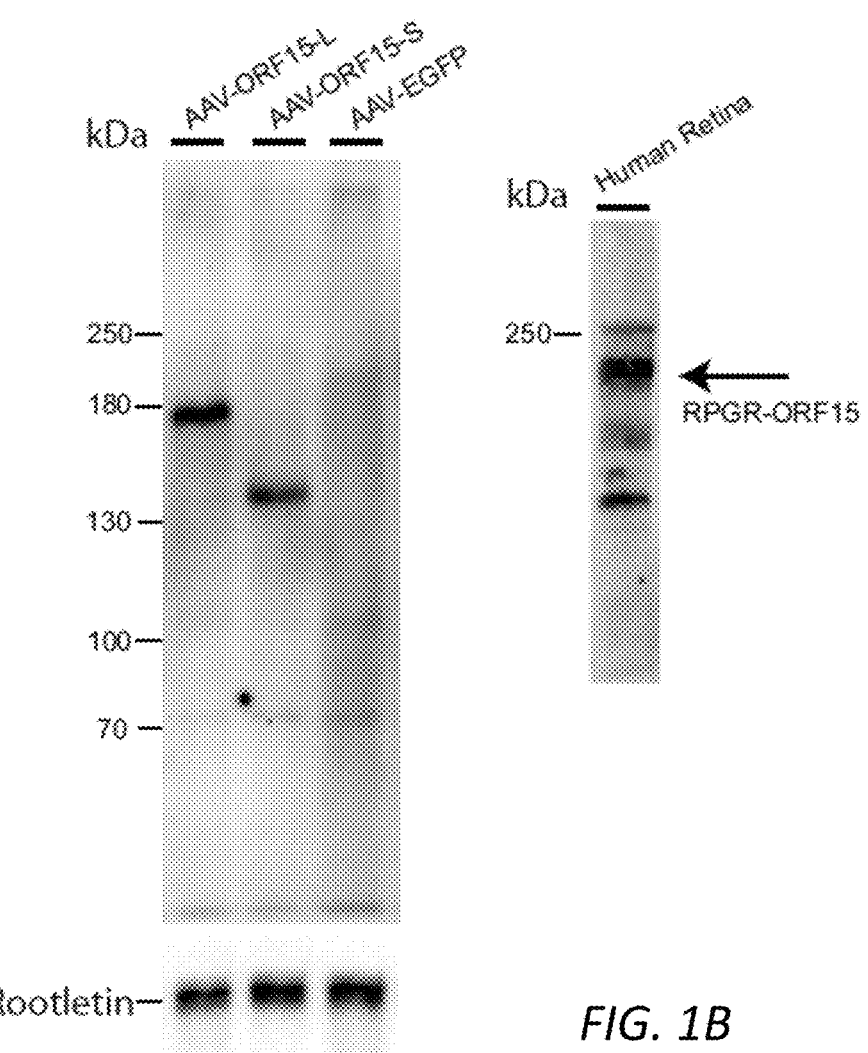

We constructed two human RPGR ORF15 replacement genes, one with an in frame deletion of 126 codons (the long form, ORF15-L) and the other with an in frame deletion of 314 codons (the short form, ORF15-S). Both were inserted into an AAV8 vector under the control of a human rhodopsin kinase promoter (FIG. 1A) (Khani and others 2007; Sun and others 2010). Subretinal delivery of the two human RPGR ORF15 replacement genes (left eyes) led to the production of recombinant RPGR proteins. By western blotting, 2 weeks following AAV vector administration, the long form of ORF15 produced an approximately 160-kD protein while the short form of ORF15 produced an approximately 125-kD protein. Both protein products were smaller than native ORF15 seen in human retinal tissue (approximately 200 kD) (FIGS. 1B, C). Both forms of replacement ORF15 appeared as a single band when probed with an antibody against the C-terminus of human RPGR. Under our experimental conditions and the dosages given, the expression levels of ORF15-S and ORF15-L were comparable. Control eyes (right eyes) received AAV-GFP.

Figure 2A:
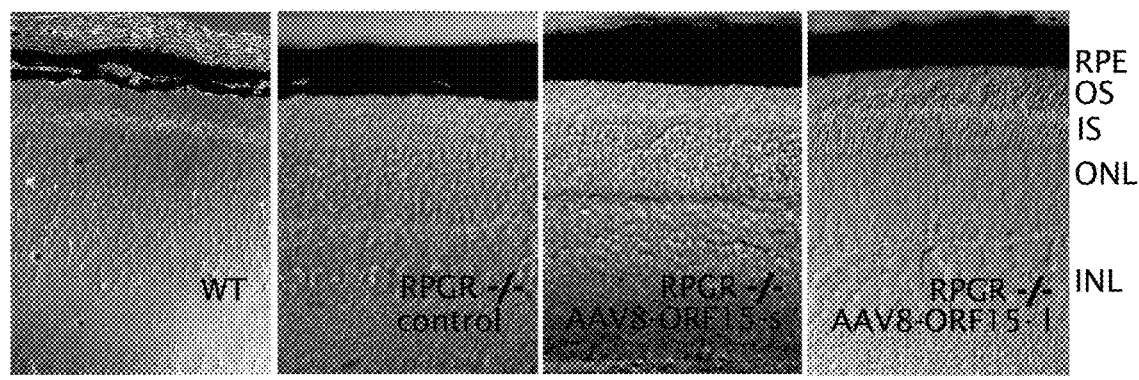

Both forms of ORF15 could be seen in the retina of RPGR$^{-/-}$ mice by immunofluorescence staining of unfixed cryosections (3 weeks following subretinal injections) and correctly localized to the layer in between the inner and outer segments where the connecting cilia reside. However, the short form (AAV8-ORF15-s) gave much weaker signals (FIG. 2A) than the long form (AAV8-ORF15-l). In well-transduced retinal areas the signal from the long form treated retinas appeared indistinguishable from the WT signal (FIGS. 2A, B). Double-labeling with an antibody for the ciliary rootlets, which originate from the proximal ends of basal bodies and extend toward the cell interior and thus serve as an excellent marker for the ciliary region (Hong and others 2003; Yang and others 2002), confirmed the correct subcellular localization of the recombinant RPGR to the connecting cilia (FIG. 2B). In contrast to the similarity in protein expression level determined by western blotting, only the long form of ORF15 appeared to have a robust signal in every CC matching the number of rootlets, whereas in the short form treated retinas, many rootlets did not have an RPGR signal at their distal ends. FIG. 2C shows a bar graph representing RPGR label counts relative to the counts of rooteletin fibers in Rpgr−/− mouse retinas treated with either the long or short form of human ORF15 as well as in untreated wildtype mouse retinas. There was no difference in the mean ratios (RPGR signal count divided by Rootletin fiber count) for the ORF15 long form versus the wild type (Dunnett's method, p=0.24) but a significantly lower mean ratio for the ORF15 short form versus the wildtype (p=0.0019).

Figure 2D:
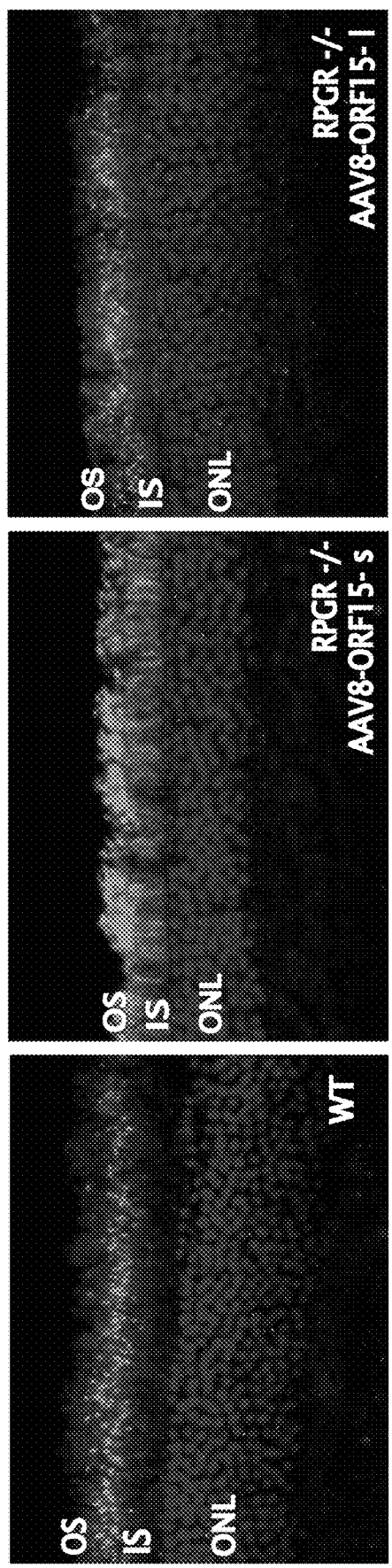

Given the similar level of expression by immunoblotting, this disparity in protein localization at the connecting cilium suggested that perhaps some fraction of the short form of ORF15 might have mislocalized elsewhere within the photoreceptors. Further analysis by immunostaining of fixed retinal sections, which afforded better preservation of tissues at the expense of signal strength, revealed a pattern of ORF15 mislocalized to photoreceptor inner and outer segments for the short form of ORF15 (FIG. 2D). No mislocalization was seen for the long form of ORF15 which had a staining pattern similar to WT. Thus, the lack of staining for the short form RPGR at the CC is due to a reduced ability to localize or be confined at this subcellular compartment, rather than a lower level of expression overall.

Example 2

Figure 3:
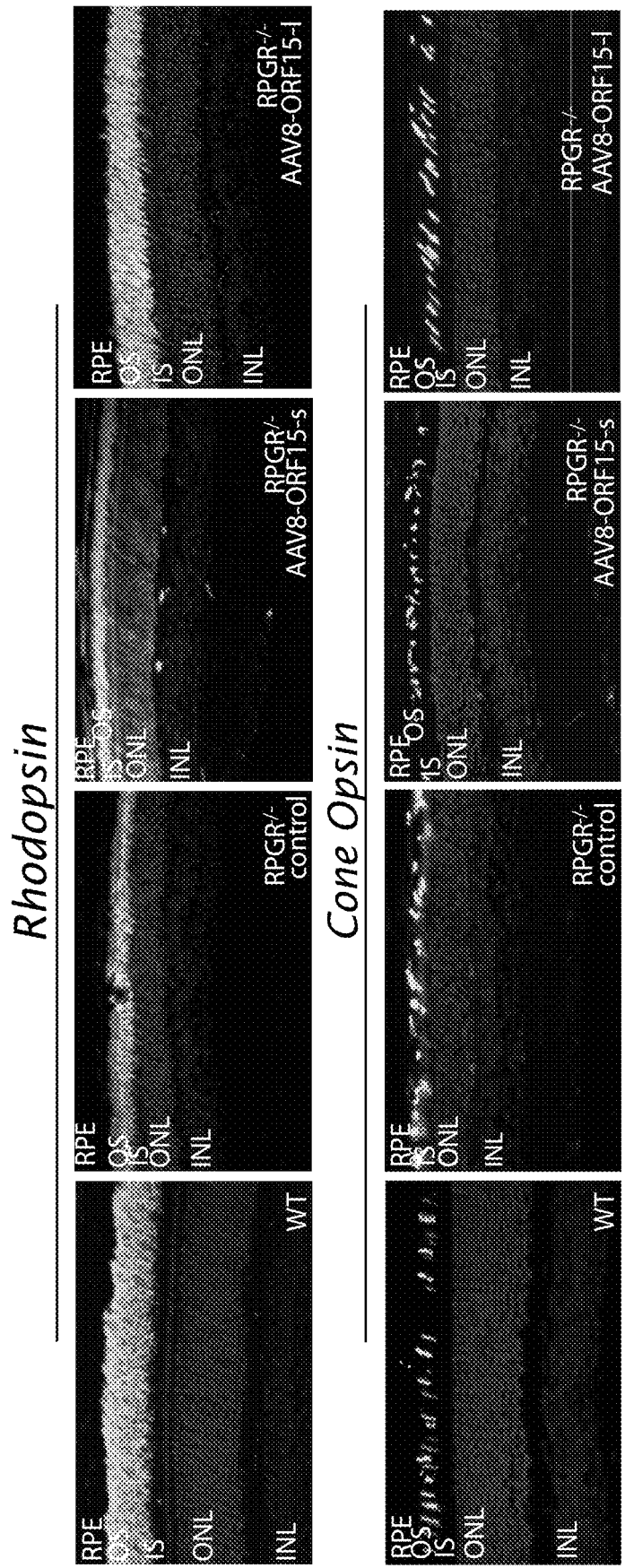
FIG. 3. Immunohistochemical (yellow in original) analyses of rod and cone photoreceptors in treated (short and long form of ORF15) and control RPGR-/- mouse retinas at age 13 months (6-months post injection). In the RPGR-/- mouse retina treated with the short form of ORF15 (AAV8-ORF15-s), rhodopsin and cone opsin (mixed S & M cones in the inferior retina) mislocalization staining patterns are virtually indistinguishable from those seen in the control retina. Note the cone opsin mislocalization in the inner segments and synaptic layer in both of these mouse retinas. Similarly, rod and cone outer segments are shortened and disorganized with a reduced outer nuclear layer compared to an age matched wt retina. In contrast, in the RPGR-/- mouse retina treated with the long form of ORF15 (AAV8-ORF15-l) rhodopsin shows outer segment partitioning similar to WT mouse retina. Also in the ORF15 long form treated retina rod outer segments are longer and well organized and the ONL is thicker compared with the control retina. Cone opsin staining shows more numerous cone photoreceptors with elongated and well-organized outer segments in the ORF15 long form treated RPGR-/- mouse retina compared with control.

Human ORF15-l (Long Form) Expression in RPGR Null Mice Promotes Rod and Cone Survival To investigate the therapeutic efficacy of the two replacement genes, we evaluated RPGR$^{-/-}$ mouse photoreceptors by immunostaining to look for signs of improvement in rod and cone morphology. By 13 months of age (6 months post treatment) there was no obvious difference in rod or cone morphology observed with the short form of human ORF15 (FIG. 3); both control and ORF15 short form treated eyes had the typical degenerative appearance for this age. Rod and cone outer segments were shortened and disorganized compared to WT eyes with rod opsin mislocalization seen throughout the outer nuclear layer and cone opsin mislocalization additionally in the synaptic layer. The outer nuclear layer, in control and ORF15 short form treated eyes, was also comparably reduced in thickness.

In contrast, eyes treated with the long form of human ORF15 had rhodopsin expression in rods that was properly partitioned to the outer segments with no obvious signs of mislocalization. Similarly, cone opsin mislocalization was rare in these eyes treated with the longer ORF15 construct. In addition, ORF15-l treated eyes were found to have more rod and cone cells (with nearly normal-appearing outer segments) than control or ORF15-S treated eyes.

Figure 4A:
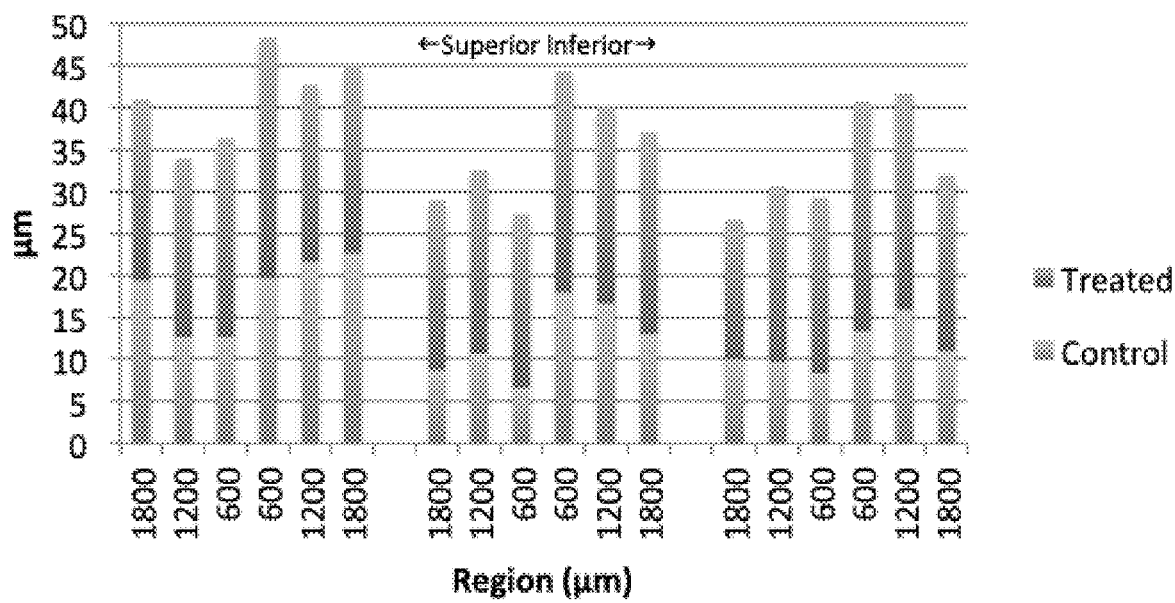
FIGS. 4A-4B. Rescue of photoreceptor cells following treatment with RPGR ORF15-l in RPGR-/- mice.
Figure 4A:
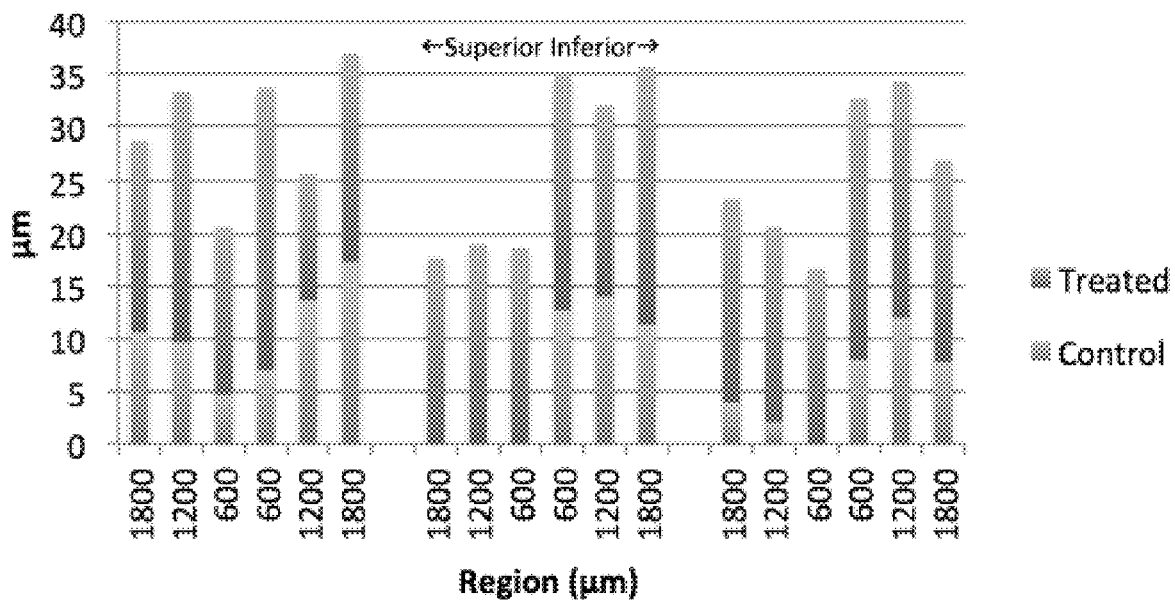

Based on these findings longitudinal studies were carried out in mice treated with the long form of ORF15. To quantify the extent of rescue in ORF15-l treated eyes relative to the control eyes, we measured the thickness of the outer nuclear layer (ONL) and the length of photoreceptor inner/outer segments in fellow eyes of 3 Rpgr$^{-/-}$ mice. These were measured in 3 regions of the superior hemisphere and in 3 regions of the inferior hemisphere, each region separated by 600 µm and beginning 600 µm to either side of the optic nerve head along the vertical meridian; Repeated-measures full-factorial regression at ages 11 months and 18 months was used to identify differences by eye, hemisphere, and region as main effects, as well as their cross-products to determine whether a treatment effect varied geographically. At 11 months of age, ONL thickness was normally distributed but inner segment/outer segment length was not (Shapiro-Wilk W goodness of fit test, p=0.016); at 18 months of age, neither ONL thickness nor inner segment/outer segment length was normally distributed (p=0.0011 and p=0.0002, respectively). At 11 months of age mean ONL thickness was significantly greater for treated eyes (48.0 µm) than for control eyes (38.0 µm, p=0.0015); mean inner segment/outer segment length was also significantly greater for treated eyes (45.1 µm) than for control eyes (29.5 µm, p<0.0001, p<0.0001 for normalized ranks). The treatment benefits with respect to ONL thickness and IS/OS length were comparable for the inferior and superior hemispheres at this age. At 18 months of age the differences in retinal morphology between fellow eyes were even more marked: mean ONL thickness was 22.8 µm for treated eyes and 13.7 µm for control eyes (p<0.0001, p<0.0001 for normalized ranks), while mean inner segment/outer segment length was 19.8 µm for treated eyes and 7.3 µm for control eyes (p<0.0001, p<0.0001 for normalized ranks). At this age we initially observed that the treatment benefit for IS/OS length was significantly greater in the superior retina than in the inferior retina at 18 months (p=0.0036), but this did not hold up after converting length to normalized ranks (p=0.17). FIG. 4A illustrates ONL thickness and IS/OS length by region for treated and control eyes in the three mice at 18 months of age.

Figure 4B:
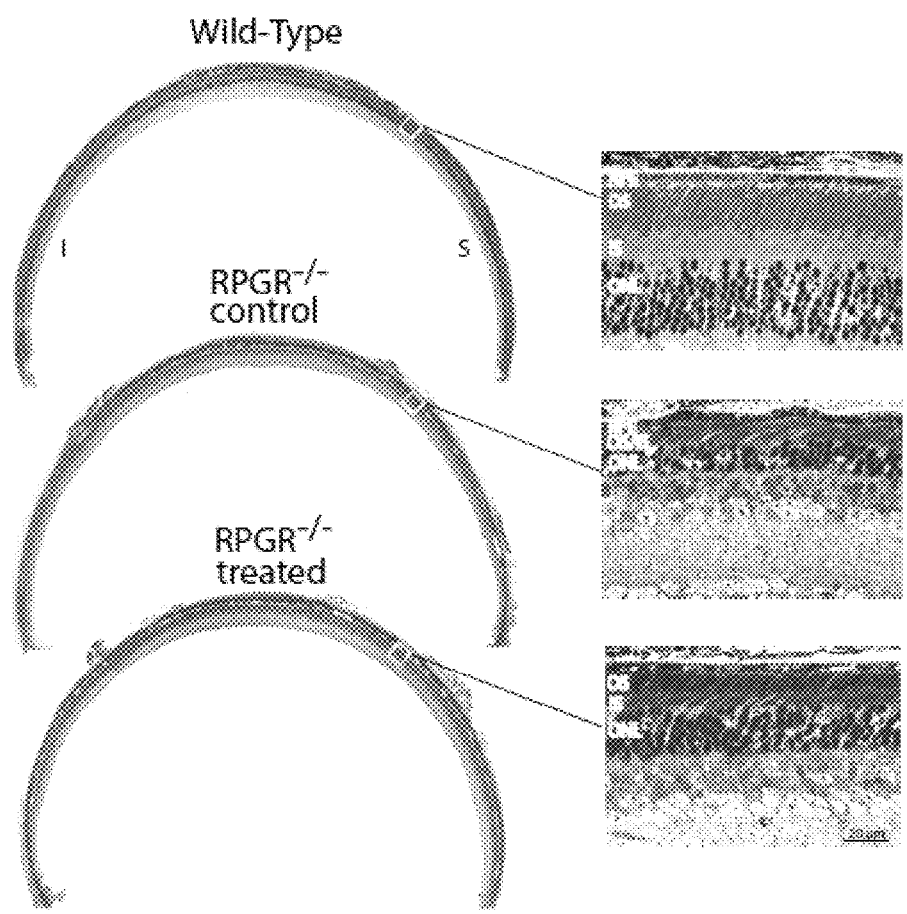

FIG. 4B shows representative light micrographs taken from a representative ORF15-L treated and fellow control eye at 18 months of age. In the control retina, the best-preserved area has only about 2-3 rows of loosely arranged photoreceptor nuclei with shortened and disorganized photoreceptor inner/outer segments. Note that the margins of the inner and outer segments are no longer distinct. The treated retina, on the other hand, has about 5-6 rows of photoreceptor cells throughout, with longer, better organized, and distinct inner and outer segments.

Example 3

Human RPGR ORF15 Long-Form Expression Improves Rod and Cone Function

Retinal function as monitored by full-field rod and cone ERGs was evaluated in a cohort (n=22) of RPGR$^{-/-}$ mice from 9-months to 18-months of age. Mice received treatment between 3 and 7 months of age, and follow-up ERGs were recorded no sooner than 6-months following injection. FIG. 5A shows rod and cone ERG amplitudes by eye for 16 mice who were tested between 11 and 14 months of age. Control eyes (OD) showed disproportionate loss of cone b-wave amplitude relative to rod b-wave amplitude compared with the lower limits for wild-type mice, as previously observed in this murine model of RPGR$^{-/-}$ mice and evidence for a cone-rod degeneration. In every case but one, the treated eye (OS) had a larger ERG a-wave and b-wave amplitude compared with the fellow control eye (OD), demonstrating improvement of rod and cone photoreceptor function. In fact, more than half of the treated eyes (9/16) had rod b-wave amplitudes that were at or above the lower limit of age-matched WT values (dotted line). Geometric mean values for rod ERG a-wave and b-wave amplitude were 121 µV OS and 65 µV OD for the a-wave and 482 µV OS and 267 µV OD for the b-wave. Mean cone ERG b-wave amplitudes was 22 µV OS and 11 µV OD. These data show an 81-86% improvement of rod function and a 100% improvement of cone function with AAV-ORF15 treatment for this age range.

Figure 5B:
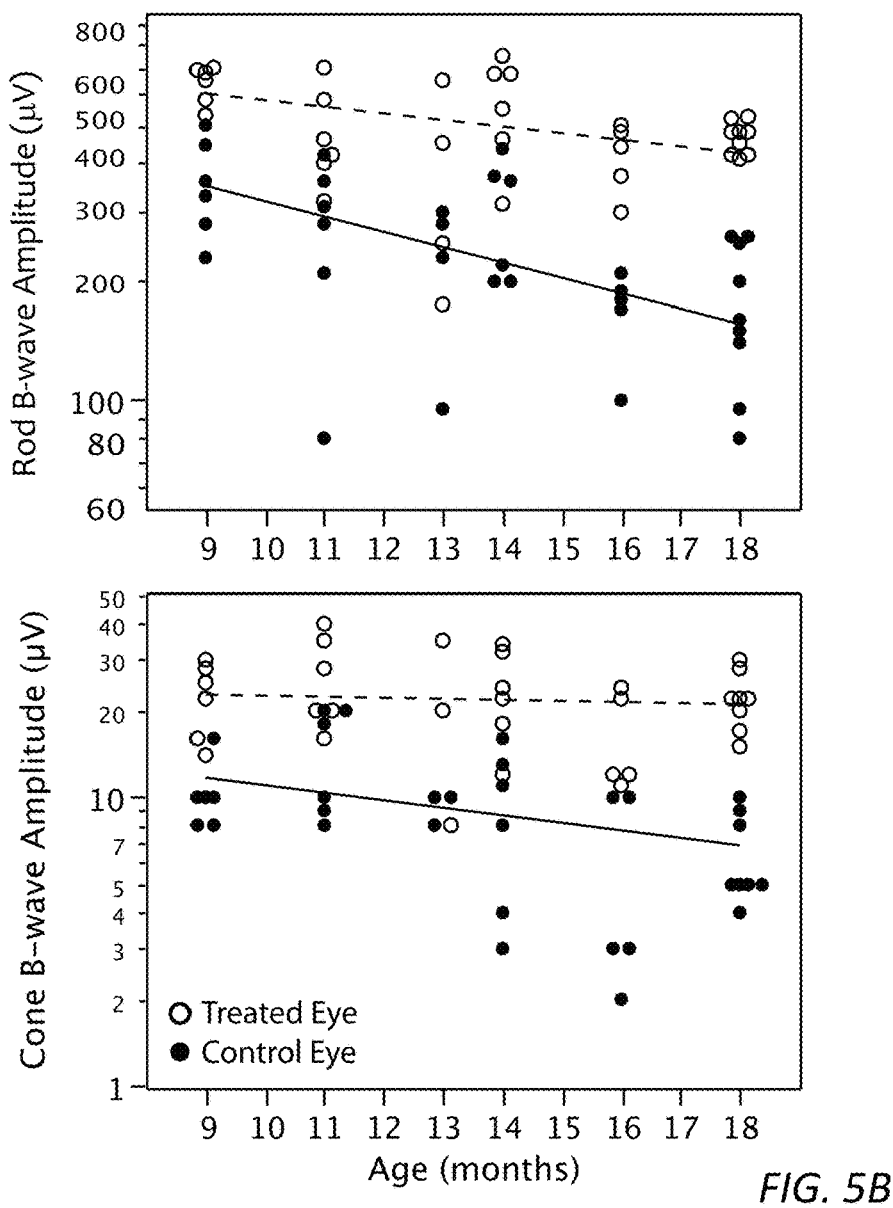
(FIG. 5B) Scatterplots of ERG amplitude for 22 RPGR-/- mice between 9 and 18 months of age on a log scale for the dark-adapted (rod) b-wave (upper graph) and light-adapted (cone) b-wave (lower graph). Data points have been shifted slightly horizontally for each age group to minimize data overlap. The regression lines for treated and control eyes were fitted by repeated measures longitudinal regression using PROC MIXED of SAS based on all available data.

In the full cohort of 22 mice, we used repeated measures longitudinal regression to compare rates of change for rod and cone b-wave amplitudes by eye (FIG. 5B). Estimated mean rates of change were −8.6%/month for rod b-wave amplitude of the control eyes and −3.8%/month for rod b-wave amplitude of the treated eyes; the difference between these two means was significant (p=0.0001). Estimated mean rates of change were −5.8%/month for cone b-wave amplitude of the control eyes and −0.8%/month for cone b-wave amplitude of the treated eyes; the difference between these two means was also significant (p<0.0001). In addition, the decline in cone b-wave amplitude for the treated eyes was found to be not significantly different from zero (p=0.54), indicating stability in cone function with no observable progression.

Figure 5C:
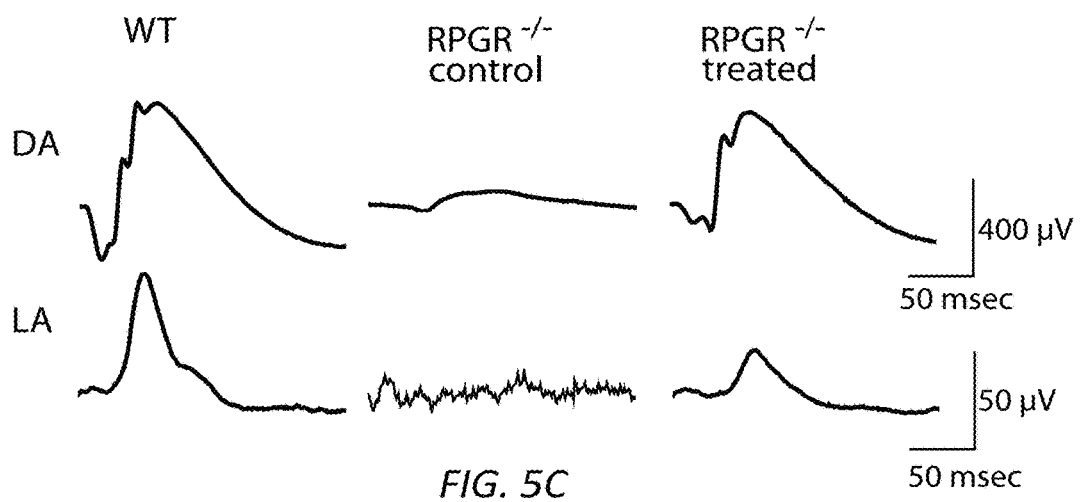
(FIG. 5C) Representative Dark-adapted (DA) and Light-adapted (LA) ERG waveforms from a pair of ORF15-l treated and fellow control RPGR-/- eyes at 18 months of age. WT (age-matched) ERG waveforms are shown for comparison. The control eye has severely reduced or nearly extinguished rod and cone ERGs, respectively, at this age. The treated eye, however, still has substantial rod and cone function at this time point that are approximately 70% and 35% of WT values, respectively.

Representative rod and cone ERGs are shown in FIG. 5C to illustrate waveforms in treated and control eyes, including a WT, at 18 months of age (the final time point). Rod function in control eyes at this age is severely reduced (by 75%, on average), while cone function is minimal and in some cases virtually non-detectable. In contrast, treated eyes at this time point still have substantial rod and cone function although below those seen in WT eyes.

REFERENCES

ACLAND G M, AGUIRRE G D, RAY J, ZHANG Q, et al. (2001). Gene therapy restores vision in a canine model of childhood blindness. Nat Genet 28, 92-5.

ALEXANDER J J, UMINO Y, EVERHART D, CHANG B, et al. (2007). Restoration of cone vision in a mouse model of achromatopsia. Nat Med 13, 685-7.

ALI R R, SARRA G M, STEPHENS C, ALWIS M D, et al. (2000). Restoration of photoreceptor ultrastructure and function in retinal degeneration slow mice by gene therapy. Nat Genet 25, 306-10.

ALLOCCA M, MUSSOLINO C, GARCIA-HOYOS M, SANGES D, et al. (2007). Novel adeno-associated virus serotypes efficiently transduce murine photoreceptors. J Virol 81, 11372-80.

BADER I, BRANDAU O, ACHATZ H, APFELSTEDT-SYLLA E, et al. (2003). X-linked retinitis pigmentosa: RPGR mutations in most families with definite X linkage and clustering of mutations in a short sequence stretch of exon ORF15. Invest Ophthalmol Vis Sci 44, 1458-63.

BAINBRIDGE J W, SMITH A J, BARKER S S, ROBBIE S, et al. (2008). Effect of gene therapy on visual function in Leber's congenital amaurosis. N Engl J Med 358, 2231-9.

BELTRAN W A, CIDECIYAN A V, LEWIN A S, IWABE S, et al. (2012). Gene therapy rescues photoreceptor blindness in dogs and paves the way for treating human X-linked retinitis pigmentosa. Proc Natl Acad Sci USA 109, 2132-7.

BERSON E L. (1993). Retinitis pigmentosa. The Friedenwald Lecture. Invest Ophthalmol Vis Sci 34, 1659-76.

BOYLAN J P, WRIGHT A F. (2000). Identification of a novel protein interacting with RPGR. Hum Mol Genet 9, 2085-2093.

BRANHAM K, OTHMAN M, BRUMM M, KAROUKIS A J, et al. (2012). Mutations in RPGR and RP2 Account for 15% of Males with Simplex Retinal Degenerative Disease. Invest Ophthalmol Vis Sci 53, 8232-7.

BREUER D K, YASHAR B M, FILIPPOVA E, HIRIYANNA S, et al. (2002). A comprehensive mutation analysis of RP2 and RPGR in a North American cohort of families with X-linked retinitis pigmentosa. Am J Hum Genet 70, 1545-54.

CHURCHILL J D, BOWNE S J, SULLIVAN L S, LEWIS R A, et al. (2013). Mutations in the X-linked retinitis pigmentosa genes RPGR and RP2 found in 8.5% of families with a provisional diagnosis of autosomal dominant retinitis pigmentosa. Invest Ophthalmol Vis Sci 54, 1411-6.

CIDECIYAN A V, ALEMAN T S, BOYE S L, SCHWARTZ S B, et al. (2008). Human gene therapy for RPE65 isomerase deficiency activates the retinoid cycle of vision but with slow rod kinetics. Proc Natl Acad Sci USA 105, 15112-7.

HONG D H, LI T. (2002). Complex expression pattern of RPGR reveals a role for purine-rich exonic splicing enhancers. Invest Ophthalmol Vis Sci 43, 3373-82.

HONG D H, PAWLYK B, SOKOLOV M, STRISSEL K J, et al. (2003). RPGR isoforms in photoreceptor connecting cilia and the transitional zone of motile cilia. Invest Ophthalmol Vis Sci 44, 2413-21.

HONG D H, PAWLYK B S, ADAMIAN M, SANDBERG M A, et al. (2005). A single, abbreviated RPGR-ORF15 variant reconstitutes RPGR function in vivo. Invest Ophthalmol Vis Sci 46, 435-41.

HONG D H, PAWLYK B S, SHANG J, SANDBERG M A, et al. (2000). A retinitis pigmentosa GTPase regulator (RPGR)-deficient mouse model for X-linked retinitis pigmentosa (RP3). Proc Natl Acad Sci USA 97, 3649-54.

HONG D H, YUE G, ADAMIAN M, LI T. (2001). Retinitis pigmentosa GTPase regulator (RPGR)-interacting protein is stably associated with the photoreceptor ciliary axoneme and anchors RPGR to the connecting cilium. J Biol Chem 276, 12091-12099.

JACOBI F K, KARRA D, BROGHAMMER M, BLIN N, et al. (2005). Mutational risk in highly repetitive exon ORF15 of the RPGR multidisease gene is not associated with haplotype background. Int J Mol Med 16, 1175-8.

KARRA D, JACOBI F K, BROGHAMMER M, BLIN N, et al. (2006). Population haplotypes of exon ORF15 of the retinitis pigmentosa GTPase regulator gene in Germany: implications for screening for inherited retinal disorders. Mol Diagn Ther 10, 115-23.

KHANI S C, PAWLYK B S, BULGAKOV O V, KASPEREK E, et al. (2007). AAV-Mediated Expression Targeting of Rod and Cone Photoreceptors with a Human Rhodopsin Kinase Promoter. Invest Ophthalmol Vis Sci 48, 3954-61.

KOMAROMY A M, ALEXANDER J J, ROWLAN J S, GARCIA M M, et al. (2010). Gene therapy rescues cone function in congenital achromatopsia. Hum Mol Genet 19, 2581-93.

LHERITEAU E, LIBEAU L, STIEGER K, DESCHAMPS J Y, et al. (2009). The RPGRIP1-deficient dog, a promising canine model for gene therapy. Mol Vis 15, 349-61.

MACLAREN R E, GROPPE M, BARNARD A R, COTTRIALL C L, et al. (2014). Retinal gene therapy in patients with choroideremia: initial findings from a phase 1/2 clinical trial. Lancet.

MAGUIRE A M, SIMONELLI F, PIERCE E A, PUGH E N, JR., et al. (2008). Safety and efficacy of gene transfer for Leber's congenital amaurosis. N Engl J Med 358, 2240-8.

NATKUNARAJAH M, TRITTIBACH P, MCINTOSH J, DURAN Y, et al. (2008). Assessment of ocular transduction using single-stranded and self-complementary recombinant adeno-associated virus serotype 2/8. Gene Ther 15, 463-7.

PANG J J, LEI L, DAI X, SHI W, et al. (2012). AAV-mediated gene therapy in mouse models of recessive retinal degeneration. Curr Mol Med 12, 316-30.

PAWLYK B S, BULGAKOV O V, LIU X, XU X, et al. (2010). Replacement gene therapy with a human RPGRIP1 sequence slows photoreceptor degeneration in a murine model of Leber congenital amaurosis. Hum Gene Ther 21, 993-1004.

PAWLYK B S, SMITH A J, BUCH P K, ADAMIAN M, et al. (2005). Gene replacement therapy rescues photoreceptor degeneration in a murine model of Leber congenital amaurosis lacking RPGRIP. Invest Ophthalmol Vis Sci 46, 3039-45.

PELLETIER V, JAMBOU M, DELPHIN N, ZINO-VIEVA E, et al. (2007). Comprehensive survey of mutations in RP2 and RPGR in patients affected with distinct retinal dystrophies: genotype-phenotype correlations and impact on genetic counseling. Hum Mutat 28, 81-91.

ROEPMAN R, BERNOUD-HUBAC N, SCHICK D E, MAUGERI A, et al. (2000). The retinitis pigmentosa GTPase regulator (RPGR) interacts with novel transport-like proteins in the outer segments of rod photoreceptors. Hum Mol Genet 9, 2095-2105.

SANDBERG M A, ROSNER B, WEIGEL-DIFRANCO C, DRYJA T P, et al. (2007). Disease course of patients with X-linked retinitis pigmentosa due to RPGR gene mutations. Invest Ophthalmol Vis Sci 48, 1298-304.

SUN X, PAWLYK B, XU X, LIU X, et al. (2010). Gene therapy with a promoter targeting both rods and cones rescues retinal degeneration caused by AIPL1 mutations. Gene Ther 17, 117-131.

TAN M R, SMITH A J, PAWLYK B, XU X, et al. (2009). Gene therapy for retinitis pigmentosa and Leber congenital amaurosis caused by defects in AIPL1: effective rescue of mouse models of partial and complete Aipl1 deficiency using AAV2/2 and AAV2/8 vectors. Hum Mol Genet.

THOMPSON D A, KHAN N W, OTHMAN M I, CHANG B, et al. (2012). Rd9 is a naturally occurring mouse model of a common form of retinitis pigmentosa caused by mutations in RPGR-ORF15. PLoS One 7, e35865.

VERVOORT R, LENNON A, BIRD A C, TULLOCH B, et al. (2000). Mutational hot spot within a new RPGR exon in X-linked retinitis pigmentosa. Nature Genetics 25, 462-466.

VERVOORT R, WRIGHT A F. (2002). Mutations of RPGR in X-linked retinitis pigmentosa (RP3). Hum Mutat 19, 486-500.

YANG J, LIU X, YUE G, ADAMIAN M, et al. (2002). Rootletin, a novel coiled-coil protein, is a structural component of the ciliary rootlet. J Cell Biol 159, 431-440.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating a human subject who has X-linked Retinitis Pigmentosa (XLRP) or another ophthalmological condition due to a loss-of-function mutation in the gene encoding the retinitis pigmentosa GTPase regulator (RPGR) protein, the method comprising administering to an eye of the subject a nucleic acid encoding an abbreviated human RPGR protein, wherein the abbreviated human RPGR protein comprises SEQ ID NO:2.

2. A method of treating a human subject who has X-linked Retinitis Pigmentosa (XLRP) or another ophthalmological condition due to a loss-of-function mutation in the gene encoding the retinitis pigmentosa GTPase regulator (RPGR) protein, the method comprising administering to an eye of the subject a viral vector comprising a nucleic acid encoding an abbreviated human RPGR protein, wherein the abbreviated human RPGR protein comprises SEQ ID NO:2.

3. The method of claim 2, wherein the nucleic acid is under the control of a human rhodopsin kinase (hRK) promoter.

4. The method of claim 3, wherein the hRK promoter comprises SEQ ID NO:5.

5. The method of claim 2, wherein the nucleic acid comprises SEQ ID NO:1.

6. The method of claim 2, comprising administering the nucleic acid in a dose of about $2\times10^{10}$ vg/mL, a dose of about $2\times10^{11}$ vg/mL, or a dose of about $2\times10^{12}$ vg/mL.

7. The method of claim 2, wherein the nucleic acid is administered into the subretinal space.

8. The method or use of claim 7, wherein a micro injection cannula is inserted into the subretinal space, temporal to the optic nerve and just above the major arcade vessels, so that fluid flow can be directed towards the macula.

9. A nucleic acid encoding an abbreviated human RPGR protein, wherein the nucleic acid encodes a protein comprising SEQ ID NO:2.

10. The nucleic acid of claim 9, wherein the nucleic acid is under the control of a human rhodopsin kinase (hRK) promoter.

11. The nucleic acid of claim 10, wherein the hRK promoter comprises SEQ ID NO:5.

12. The nucleic acid of claim 10, wherein the hRK promoter consists essentially of SEQ ID NO:5.

13. A viral vector comprising the nucleic acid of claim 9.

14. The viral vector of claim 13, wherein the vector is an adeno-associated viral vector.

15. The viral vector of claim 14, wherein the adeno-associated viral vector is AAV-2 or AAV-8.

16. An isolated host cell comprising the viral vector of claim 13.

17. The isolated host cell of claim 16, wherein the cell expresses the abbreviated human RPGR protein.

18. The method of claim 2, wherein the viral vector is an adeno-associated viral vector.

19. The method of claim 18, wherein the adeno-associated viral vector is AAV-2 or AAV-8.

20. The method of claim 1, wherein the abbreviated human RPGR protein consists of SEQ ID NO:2.

21. The method of claim 2, wherein the abbreviated human RPGR protein consists of SEQ ID NO:2.

22. The viral vector of claim 14, wherein the adeno-associated viral vector is AAV2/8.

23. The method of claim 18, wherein the adeno-associated viral vector is AAV2/8.

* * * * *